United States Patent
Manwaring et al.

(10) Patent No.: US 11,266,459 B2
(45) Date of Patent: Mar. 8, 2022

(54) SEALING AND/OR CUTTING INSTRUMENT

(71) Applicant: Domain Surgical, Inc., Salt Lake City, UT (US)

(72) Inventors: Kim H. Manwaring, Phoenix, AZ (US); David J. McNally, Salt Lake City, UT (US); Philip Eggers, Cottonwood Heights, UT (US); Preston Manwaring, Farmington, UT (US); Mark Stringham, Kearns, UT (US); Kent Beck, Layton, UT (US); David Wright, Littleton, CO (US); Josh Middel, Littleton, CO (US)

(73) Assignee: Domain Surgical, Inc., Billerica, MA (US)

( * ) Notice: Subject to any disclaimer, the term of this patent is extended or adjusted under 35 U.S.C. 154(b) by 1105 days.

(21) Appl. No.: 15/344,592

(22) Filed: Nov. 7, 2016

(65) Prior Publication Data

US 2017/0209200 A1  Jul. 27, 2017
US 2020/0289186 A9  Sep. 17, 2020

Related U.S. Application Data

(63) Continuation of application No. 13/614,226, filed on Sep. 13, 2012, now Pat. No. 9,526,558.
(Continued)

(51) Int. Cl.
*A61B 18/08*  (2006.01)
*A61B 18/10*  (2006.01)
(Continued)

(52) U.S. Cl.
CPC ............ *A61B 18/085* (2013.01); *A61B 18/10* (2013.01); *A61B 2017/00876* (2013.01);
(Continued)

(58) Field of Classification Search
CPC .................................................. A61B 18/085
See application file for complete search history.

(56) References Cited

U.S. PATENT DOCUMENTS

| 300,155 A | 6/1884 | Starr |
| 770,368 A | 9/1904 | Heath |

(Continued)

FOREIGN PATENT DOCUMENTS

| EP | 0 033 958 A1 | 8/1981 |
| EP | 0 130 671 A2 | 1/1985 |

(Continued)

OTHER PUBLICATIONS

De Cupis et al., "Electromagnetic Probes for Living Tissue Cauterization," *URSI International Symposium on Electromagnetic Theory*, Pisa, Italy, May 23-27, 2004, pp. 489-491.
(Continued)

*Primary Examiner* — Rex R Holmes
*Assistant Examiner* — Jennifer L Ghand
(74) *Attorney, Agent, or Firm* — Cozen O'Connor

(57) ABSTRACT

A sealing and/or cutting instrument having a thermally active surface or element which may be used to seal and then cut tissue, ducts, vessels, etc., apart. The instrument may include a thermally active surface or element comprised of a conductor covered with a ferromagnetic material. The instrument may contact tissue with one or more surfaces comprised of a non-stick material. A sensor in communication with the instrument may be used to monitor a therapeutic procedure and signal when sealing and/or cutting of a tissue is complete.

17 Claims, 29 Drawing Sheets

Related U.S. Application Data

(60) Provisional application No. 61/534,322, filed on Sep. 13, 2011, provisional application No. 61/534,047, filed on Sep. 13, 2011.

(51) Int. Cl.
  *A61B 17/00*  (2006.01)
  *A61B 18/00*  (2006.01)

(52) U.S. Cl.
  CPC ................ *A61B 2018/0063* (2013.01); *A61B 2018/00148* (2013.01); *A61B 2018/00428* (2013.01); *A61B 2018/00607* (2013.01); *A61B 2018/00642* (2013.01); *A61B 2018/00678* (2013.01); *A61B 2018/00726* (2013.01); *A61B 2018/00791* (2013.01); *A61B 2018/00851* (2013.01); *A61B 2018/00875* (2013.01); *A61B 2018/00898* (2013.01)

(56) References Cited

U.S. PATENT DOCUMENTS

| | | |
|---|---|---|
| 1,104,053 A | 7/1914 | Lea |
| 1,280,052 A | 9/1918 | Lidberg |
| 1,335,987 A | 4/1920 | Reid et al. |
| 1,366,231 A | 1/1921 | Winter et al. |
| 1,401,104 A | 12/1921 | Kruesheld et al. |
| 1,794,296 A | 2/1931 | Hyams |
| 2,027,854 A | 1/1936 | Breth et al. |
| 2,050,904 A | 8/1936 | Trice |
| 2,120,598 A | 6/1938 | Beuoy |
| 2,250,602 A | 7/1941 | Pierce |
| 2,278,633 A | 4/1942 | Bagnall |
| 2,375,154 A | 5/1945 | Volterra |
| 2,412,977 A | 12/1946 | Eskin |
| 2,501,499 A | 3/1950 | Crowley |
| 2,670,425 A | 2/1954 | Stone |
| 2,735,797 A | 2/1956 | Schjeldahl |
| 2,782,290 A | 2/1957 | Lannan et al. |
| 2,831,242 A | 4/1958 | Kieffer et al. |
| 2,846,560 A | 8/1958 | Jacoby et al. |
| 2,863,036 A | 12/1958 | Mitchell et al. |
| 2,947,345 A | 8/1960 | Schjeldahl |
| 2,960,592 A | 11/1960 | Pierce |
| 3,084,242 A | 4/1963 | Vogler et al. |
| 3,213,259 A | 10/1965 | Bennett et al. |
| 3,350,544 A | 10/1967 | Lennox |
| 3,352,011 A | 11/1967 | Alexander et al. |
| 3,400,252 A | 9/1968 | Hayakawa et al. |
| 3,404,202 A | 10/1968 | Carlson et al. |
| 3,413,442 A | 11/1968 | Buiting et al. |
| 3,414,705 A | 12/1968 | Marcoux |
| 3,434,476 A | 3/1969 | Shaw et al. |
| 3,501,619 A | 3/1970 | Buiting et al. |
| 3,515,837 A | 6/1970 | Ando |
| 3,520,043 A | 7/1970 | Darling |
| 3,556,953 A | 1/1971 | Schulz |
| 3,768,482 A | 10/1973 | Shaw |
| 3,825,004 A | 7/1974 | Durden, III |
| 3,826,263 A | 7/1974 | Cage et al. |
| 3,834,392 A | 9/1974 | Lampman et al. |
| 3,978,312 A | 8/1976 | Barton et al. |
| RE29,088 E | 12/1976 | Shaw |
| 4,089,336 A | 5/1978 | Cage et al. |
| 4,091,813 A | 5/1978 | Shaw et al. |
| RE30,190 E | 1/1980 | Shaw |
| 4,185,632 A | 1/1980 | Shaw |
| 4,196,734 A | 4/1980 | Harris |
| 4,198,957 A | 4/1980 | Cage et al. |
| 4,206,759 A | 6/1980 | Shaw |
| 4,207,896 A | 6/1980 | Shaw |
| 4,209,017 A | 6/1980 | Shaw |
| 4,256,945 A | 3/1981 | Carter et al. |
| 4,359,052 A | 11/1982 | Staub |
| 4,364,390 A | 12/1982 | Shaw |
| 4,371,861 A | 2/1983 | Abdulrahman et al. |
| 4,374,517 A | 2/1983 | Hagiwara |
| RE31,723 E | 11/1984 | Shaw |
| 4,481,057 A | 11/1984 | Beard |
| 4,485,810 A | 12/1984 | Beard |
| 4,492,231 A | 1/1985 | Auth |
| 4,493,320 A | 1/1985 | Treat |
| 4,523,084 A | 6/1985 | Tamura et al. |
| 4,549,073 A | 10/1985 | Tamura et al. |
| 4,600,018 A | 7/1986 | James et al. |
| 4,622,966 A | 11/1986 | Beard |
| 4,658,819 A | 4/1987 | Harris et al. |
| 4,658,820 A | 4/1987 | Klicek |
| 4,701,587 A | 10/1987 | Carter et al. |
| 4,752,673 A | 6/1988 | Krumme |
| 4,807,620 A | 2/1989 | Strul et al. |
| 4,839,501 A | 6/1989 | Cowell |
| 4,848,337 A | 7/1989 | Shaw et al. |
| 4,860,745 A | 8/1989 | Farin et al. |
| 4,877,944 A | 10/1989 | Cowell et al. |
| 4,914,267 A | 4/1990 | Derbyshire |
| 4,915,100 A | 4/1990 | Green |
| 4,927,413 A | 5/1990 | Hess |
| 4,938,761 A | 7/1990 | Ensslin |
| 5,003,991 A | 4/1991 | Takayama et al. |
| 5,047,025 A | 9/1991 | Taylor et al. |
| 5,053,595 A | 10/1991 | Derbyshire |
| 5,057,106 A | 10/1991 | Kasevich et al. |
| 5,071,419 A | 12/1991 | Rydell et al. |
| 5,087,256 A | 2/1992 | Taylor et al. |
| 5,087,804 A | 2/1992 | McGaffigan |
| 5,098,429 A | 3/1992 | Sterzer |
| 5,107,095 A | 4/1992 | Derbyshire |
| 5,182,427 A | 1/1993 | McGaffigan |
| 5,189,271 A | 2/1993 | Derbyshire |
| 5,197,649 A | 3/1993 | Bessler et al. |
| 5,203,782 A | 4/1993 | Gudov et al. |
| 5,209,725 A | 5/1993 | Roth |
| 5,211,646 A | 5/1993 | Alperovich et al. |
| 5,217,460 A | 6/1993 | Knoepfler |
| 5,300,068 A | 4/1994 | Rosar et al. |
| 5,300,750 A | 4/1994 | Carter, Jr. et al. |
| 5,308,311 A | 5/1994 | Eggers et al. |
| 5,318,564 A | 6/1994 | Eggers |
| 5,364,392 A | 11/1994 | Warner et al. |
| 5,370,645 A | 12/1994 | Klicek et al. |
| 5,370,675 A | 12/1994 | Edwards et al. |
| 5,376,094 A | 12/1994 | Kline |
| 5,382,247 A | 1/1995 | Cimino et al. |
| 5,400,267 A | 3/1995 | Denen et al. |
| 5,411,508 A | 5/1995 | Bessler et al. |
| 5,423,808 A | 6/1995 | Edwards et al. |
| 5,425,731 A | 6/1995 | Daniel et al. |
| 5,445,635 A | 8/1995 | Denen et al. |
| 5,472,443 A | 12/1995 | Cordis et al. |
| 5,475,203 A | 12/1995 | McGaffigan |
| 5,480,397 A | 1/1996 | Eggers et al. |
| 5,480,398 A | 1/1996 | Eggers |
| 5,496,312 A | 3/1996 | Klicek |
| 5,496,314 A | 3/1996 | Eggers |
| 5,507,743 A | 4/1996 | Edwards et al. |
| 5,540,679 A | 7/1996 | Fram et al. |
| 5,540,681 A | 7/1996 | Strul et al. |
| 5,542,916 A | 8/1996 | Hirsch et al. |
| 5,571,153 A | 11/1996 | Wallstén |
| 5,573,533 A | 11/1996 | Strul |
| 5,593,406 A | 1/1997 | Eggers et al. |
| 5,595,565 A | 1/1997 | Treat et al. |
| 5,611,798 A | 3/1997 | Eggers |
| 5,628,771 A | 5/1997 | Mizukawa et al. |
| 5,674,219 A | 10/1997 | Monson et al. |
| 5,707,369 A | 1/1998 | Vaitekunas et al. |
| 5,707,402 A | 1/1998 | Heim |
| 5,807,392 A | 9/1998 | Eggers |
| 5,807,393 A | 9/1998 | Williamson, IV et al. |
| 5,827,269 A | 10/1998 | Saadat |
| 5,836,874 A | 11/1998 | Swanson et al. |
| 5,836,943 A | 11/1998 | Miller, III |
| 5,843,019 A | 12/1998 | Eggers et al. |

(56) References Cited

U.S. PATENT DOCUMENTS

| | | |
|---|---|---|
| 5,855,061 A | 1/1999 | Malis et al. |
| 5,911,719 A | 6/1999 | Eggers |
| 5,951,546 A | 9/1999 | Lorentzen |
| 5,964,759 A | 10/1999 | Yamanashi et al. |
| 6,004,316 A | 12/1999 | Laufer |
| 6,006,755 A | 12/1999 | Edwards |
| 6,015,415 A | 1/2000 | Avellanet |
| 6,035,238 A | 3/2000 | Ingle et al. |
| 6,038,017 A | 3/2000 | Pinsukanjana et al. |
| 6,039,733 A | 3/2000 | Buysse et al. |
| 6,066,138 A | 5/2000 | Sheffer et al. |
| 6,161,048 A | 12/2000 | Sluijter et al. |
| 6,190,382 B1 | 2/2001 | Ormsby et al. |
| 6,210,403 B1 | 4/2001 | Klicek |
| 6,228,084 B1 | 5/2001 | Kirwan, Jr. |
| 6,241,723 B1 | 6/2001 | Heim et al. |
| 6,287,305 B1 | 9/2001 | Heim et al. |
| 6,290,697 B1 | 9/2001 | Tu et al. |
| 6,350,262 B1 | 2/2002 | Ashley |
| 6,358,273 B1 | 3/2002 | Strul et al. |
| 6,454,781 B1 | 9/2002 | Witt et al. |
| 6,533,781 B2 | 3/2003 | Heim et al. |
| 6,602,252 B2 | 8/2003 | Mollenauer |
| 6,604,003 B2 | 8/2003 | Fredricks et al. |
| 6,626,901 B1 | 9/2003 | Treat et al. |
| 6,632,182 B1 | 10/2003 | Treat |
| 6,692,489 B1 | 2/2004 | Heim et al. |
| 6,723,094 B1 | 4/2004 | Desinger |
| 6,726,683 B1 | 4/2004 | Shaw |
| 6,860,880 B2 | 3/2005 | Treat et al. |
| 6,908,463 B2 | 6/2005 | Treat et al. |
| 6,911,026 B1 | 6/2005 | Hall et al. |
| 6,912,911 B2 | 7/2005 | Oh et al. |
| 6,980,862 B2 | 12/2005 | Fredricks et al. |
| 6,980,865 B1 | 12/2005 | Wang et al. |
| 7,025,065 B2 | 4/2006 | McGaffigan et al. |
| 7,083,613 B2 | 8/2006 | Treat |
| 7,112,201 B2 | 9/2006 | Truckai et al. |
| 7,122,030 B2 | 10/2006 | Flores et al. |
| 7,164,968 B2 | 1/2007 | Treat et al. |
| 7,175,621 B2 | 2/2007 | Heim et al. |
| 7,211,079 B2 | 5/2007 | Treat |
| 7,211,080 B2 | 5/2007 | Treat et al. |
| 7,300,452 B2 | 11/2007 | Gleich |
| 7,317,275 B2 | 1/2008 | Treat |
| 7,329,255 B2 | 2/2008 | McGaffigan |
| 7,377,919 B2 | 5/2008 | Heim et al. |
| 7,435,249 B2 | 10/2008 | Buysse et al. |
| 7,473,250 B2 | 1/2009 | Makin et al. |
| 7,473,253 B2 | 1/2009 | Dycus et al. |
| 7,494,492 B2 | 2/2009 | Da Silva et al. |
| 7,528,663 B2 | 5/2009 | Naletov et al. |
| 7,533,719 B2 | 5/2009 | Hinson et al. |
| 7,540,324 B2 | 6/2009 | de Rouffignac et al. |
| 7,549,470 B2 | 6/2009 | Vinegar et al. |
| 7,553,309 B2 | 6/2009 | Buysse et al. |
| 7,556,095 B2 | 7/2009 | Vinegar |
| 7,556,096 B2 | 7/2009 | Vinegar et al. |
| 7,559,367 B2 | 7/2009 | Vinegar et al. |
| 7,559,368 B2 | 7/2009 | Vinegar et al. |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud et al. |
| 7,597,147 B2 | 10/2009 | Vitek et al. |
| 7,604,052 B2 | 10/2009 | Roes et al. |
| 7,610,962 B2 | 11/2009 | Fowler |
| 7,613,523 B2 | 11/2009 | Eggers et al. |
| 7,631,689 B2 | 12/2009 | Vinegar et al. |
| 7,631,690 B2 | 12/2009 | Vinegar et al. |
| 7,632,295 B2 | 12/2009 | Flores et al. |
| 7,635,023 B2 | 12/2009 | Goldberg et al. |
| 7,635,024 B2 | 12/2009 | Karanikas et al. |
| 7,635,025 B2 | 12/2009 | Vinegar et al. |
| 7,678,105 B2 | 3/2010 | McGreevy et al. |
| 7,699,842 B2 | 4/2010 | Buysse et al. |
| 7,702,397 B2 | 4/2010 | Fredricks et al. |
| 7,776,035 B2 | 8/2010 | Rick et al. |
| 7,828,798 B2 | 11/2010 | Buysse et al. |
| 7,871,406 B2 | 1/2011 | Nields et al. |
| 7,879,033 B2 | 2/2011 | Sartor et al. |
| 7,887,535 B2 | 2/2011 | Lands et al. |
| 7,922,713 B2 | 4/2011 | Geisel |
| 7,931,649 B2 | 4/2011 | Couture et al. |
| 7,938,779 B2 | 5/2011 | Sakurai et al. |
| 7,951,149 B2 | 5/2011 | Carlton |
| 7,951,150 B2 | 5/2011 | Johnson et al. |
| 7,959,633 B2 | 6/2011 | Sartor et al. |
| 7,963,965 B2 | 6/2011 | Buysse et al. |
| 7,972,334 B2 | 7/2011 | McGreevy et al. |
| 7,972,335 B2 | 7/2011 | McGreevy et al. |
| 7,981,113 B2 | 7/2011 | Truckai et al. |
| 8,062,290 B2 | 11/2011 | Buysse et al. |
| 8,100,896 B2 | 1/2012 | Podhajsky |
| 8,100,908 B2 | 1/2012 | McGaffigan et al. |
| 8,104,956 B2 | 1/2012 | Blaha |
| 8,105,323 B2 | 1/2012 | Buysse et al. |
| 8,211,105 B2 | 7/2012 | Buysse et al. |
| 8,241,284 B2 | 8/2012 | Dycus et al. |
| 8,287,528 B2 | 10/2012 | Wham et al. |
| 8,377,057 B2 | 2/2013 | Rick et al. |
| 8,460,870 B2 | 6/2013 | Zocchi et al. |
| 8,480,666 B2 | 7/2013 | Buysse et al. |
| 8,568,402 B2 | 10/2013 | Buysse et al. |
| 8,667,674 B2 | 3/2014 | Buysse |
| 8,672,938 B2 | 3/2014 | Buysse et al. |
| 2001/0014804 A1 | 8/2001 | Goble et al. |
| 2002/0016591 A1 | 2/2002 | Levine et al. |
| 2002/0019627 A1 | 2/2002 | Maguire et al. |
| 2002/0019644 A1 | 2/2002 | Hastings et al. |
| 2002/0026188 A1 | 2/2002 | Balbierz et al. |
| 2002/0029037 A1 | 3/2002 | Kim |
| 2002/0029062 A1 | 3/2002 | Satake |
| 2002/0068931 A1 | 6/2002 | Wong et al. |
| 2002/0087156 A1 | 7/2002 | Maguire et al. |
| 2002/0120261 A1 | 8/2002 | Morris et al. |
| 2002/0133148 A1 | 9/2002 | Daniel et al. |
| 2002/0165529 A1 | 11/2002 | Danek |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0109871 A1 | 6/2003 | Johnson et al. |
| 2003/0139741 A1 | 7/2003 | Goble et al. |
| 2003/0144660 A1 | 7/2003 | Mollenauer |
| 2003/0171747 A1 | 9/2003 | Kanehira et al. |
| 2003/0176873 A1 | 9/2003 | Chernenko et al. |
| 2003/0195499 A1 | 10/2003 | Prakash et al. |
| 2003/0199755 A1 | 10/2003 | Halperin et al. |
| 2003/0208199 A1 | 11/2003 | Keane |
| 2003/0212389 A1 | 11/2003 | Durgin et al. |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto et al. |
| 2004/0167506 A1 | 8/2004 | Chen |
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0090817 A1 | 4/2005 | Phan |
| 2005/0107776 A1 | 5/2005 | McGaffigan et al. |
| 2005/0113824 A1 | 5/2005 | Sartor et al. |

(56) References Cited

U.S. PATENT DOCUMENTS

| | | |
|---|---|---|
| 2005/0197661 A1 | 9/2005 | Carrison et al. |
| 2005/0245919 A1 | 11/2005 | van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0004356 A1 | 1/2006 | Bilski et al. |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1* | 9/2006 | Lau ................. A61B 17/29 606/45 |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2006/0287649 A1 | 12/2006 | Ormsby et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0016272 A1 | 1/2007 | Thompson et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0100405 A1 | 5/2007 | Thompson et al. |
| 2007/0106294 A1 | 5/2007 | Nesbitt |
| 2007/0127897 A1 | 6/2007 | John et al. |
| 2007/0131428 A1 | 6/2007 | Willem Cornelis den Boestert et al. |
| 2007/0173811 A1 | 7/2007 | Couture et al. |
| 2007/0208339 A1 | 9/2007 | Arts et al. |
| 2007/0219544 A1 | 9/2007 | Gowda et al. |
| 2007/0239151 A1 | 10/2007 | Atalar et al. |
| 2007/0270924 A1 | 11/2007 | McCann et al. |
| 2008/0017380 A1 | 1/2008 | Vinegar et al. |
| 2008/0033419 A1 | 2/2008 | Nields et al. |
| 2008/0035346 A1 | 2/2008 | Nair et al. |
| 2008/0035347 A1 | 2/2008 | Brady et al. |
| 2008/0035705 A1 | 2/2008 | Menotti |
| 2008/0038144 A1 | 2/2008 | Maziasz et al. |
| 2008/0077129 A1 | 3/2008 | Van Wyk et al. |
| 2008/0119841 A1 | 5/2008 | Geisel |
| 2008/0128134 A1 | 6/2008 | Mudunuri et al. |
| 2008/0135253 A1 | 6/2008 | Vinegar et al. |
| 2008/0135254 A1 | 6/2008 | Vinegar et al. |
| 2008/0142216 A1 | 6/2008 | Vinegar et al. |
| 2008/0142217 A1 | 6/2008 | Pieterson et al. |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar et al. |
| 2008/0187989 A1 | 8/2008 | McGreevy et al. |
| 2008/0217003 A1 | 9/2008 | Kuhlman et al. |
| 2008/0217016 A1 | 9/2008 | Stegemeier et al. |
| 2008/0228135 A1 | 9/2008 | Snoderly |
| 2008/0236831 A1 | 10/2008 | Hsu |
| 2008/0255642 A1 | 10/2008 | Zarins et al. |
| 2008/0277113 A1 | 11/2008 | Stegemeier et al. |
| 2008/0281310 A1 | 11/2008 | Dunning et al. |
| 2008/0281315 A1 | 11/2008 | Gines |
| 2008/0281386 A1 | 11/2008 | Herbette et al. |
| 2008/0319438 A1 | 12/2008 | DeCarlo |
| 2009/0014180 A1 | 1/2009 | Stegemeier et al. |
| 2009/0014181 A1 | 1/2009 | Vinegar et al. |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0004650 A1 | 1/2010 | Ormsby et al. |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268205 A1 | 10/2010 | Manwaring et al. |
| 2010/0268206 A1 | 10/2010 | Manwaring et al. |
| 2010/0268207 A1 | 10/2010 | Manwaring et al. |
| 2010/0268208 A1 | 10/2010 | Manwaring et al. |
| 2010/0268209 A1 | 10/2010 | Manwaring et al. |
| 2010/0268210 A1 | 10/2010 | Manwaring et al. |
| 2010/0268211 A1 | 10/2010 | Manwaring et al. |
| 2010/0268212 A1 | 10/2010 | Manwaring et al. |
| 2010/0268213 A1 | 10/2010 | Manwaring et al. |
| 2010/0268214 A1 | 10/2010 | Manwaring et al. |
| 2010/0268215 A1 | 10/2010 | Manwaring et al. |
| 2010/0268216 A1 | 10/2010 | Manwaring et al. |
| 2010/0268218 A1 | 10/2010 | Ormsby et al. |
| 2011/0004204 A1 | 1/2011 | Dodde et al. |
| 2011/0054456 A1 | 3/2011 | Thompson et al. |
| 2011/0092971 A1 | 4/2011 | Sartor et al. |
| 2011/0152857 A1 | 6/2011 | Ingle |
| 2012/0059367 A1 | 3/2012 | Buysse et al. |
| 2012/0071712 A1 | 3/2012 | Manwaring et al. |
| 2012/0071870 A1 | 3/2012 | Salahieh et al. |
| 2012/0130256 A1 | 5/2012 | Buysse et al. |
| 2012/0150170 A1 | 6/2012 | Buysse et al. |
| 2012/0226270 A1 | 9/2012 | Manwaring et al. |
| 2012/0259323 A1 | 10/2012 | Manwaring et al. |
| 2012/0296326 A1 | 11/2012 | Manwaring et al. |
| 2012/0303026 A1 | 11/2012 | Dycus et al. |
| 2012/0330295 A1 | 12/2012 | Manwaring et al. |
| 2013/0006240 A1 | 1/2013 | McNally et al. |
| 2013/0012934 A1 | 1/2013 | Manwaring et al. |
| 2013/0023866 A1 | 1/2013 | Stringham et al. |
| 2013/0041367 A1 | 2/2013 | Wham et al. |
| 2013/0158535 A1 | 6/2013 | Denis et al. |
| 2013/0197502 A1 | 8/2013 | Manwaring et al. |
| 2013/0218152 A1 | 8/2013 | Manwaring et al. |
| 2013/0226165 A1 | 8/2013 | Manwaring et al. |
| 2013/0296838 A1 | 11/2013 | Manwaring et al. |
| 2014/0052119 A1 | 2/2014 | Stewart et al. |
| 2014/0058381 A1 | 2/2014 | Wham et al. |
| 2014/0058384 A1 | 2/2014 | Buysse et al. |
| 2014/0058385 A1 | 2/2014 | Wham et al. |
| 2014/0074082 A1 | 3/2014 | Denis et al. |
| 2014/0100559 A1 | 4/2014 | Wham et al. |
| 2014/0180266 A1 | 6/2014 | Buysse et al. |
| 2015/0327907 A1 | 11/2015 | Stringham et al. |
| 2016/0030102 A1 | 2/2016 | Manwaring et al. |
| 2016/0030103 A1 | 2/2016 | Manwaring et al. |
| 2016/0192977 A1 | 7/2016 | Manwaring et al. |
| 2016/0249971 A1 | 9/2016 | Manwaring et al. |
| 2017/0189094 A9 | 7/2017 | Manwaring et al. |
| 2017/0196617 A1 | 7/2017 | Denis et al. |

FOREIGN PATENT DOCUMENTS

| | | |
|---|---|---|
| EP | 2 036 512 A1 | 3/2009 |
| EP | 2 070 486 A1 | 6/2009 |
| GB | 1 546 624 A | 5/1979 |
| GB | 2 022 974 A | 12/1979 |
| JP | 3-51179 B2 | 8/1991 |
| JP | 2558584 B2 | 11/1996 |
| JP | 10-277050 A | 10/1998 |
| RU | 2 072 118 C1 | 1/1997 |
| WO | 82/00746 A1 | 3/1982 |
| WO | 92/17121 A1 | 10/1992 |
| WO | 93/21839 A1 | 11/1993 |
| WO | 94/08524 A1 | 4/1994 |
| WO | 96/26677 A1 | 9/1996 |
| WO | 99/37227 A1 | 7/1999 |

(56) References Cited

FOREIGN PATENT DOCUMENTS

| WO | 01/06943 A1 | 2/2001 |
|---|---|---|
| WO | 2004/014217 A2 | 2/2004 |
| WO | 2004/076146 A2 | 9/2004 |
| WO | 2006/017517 A2 | 2/2006 |
| WO | 2006/029649 A1 | 3/2006 |
| WO | 2007/080578 A2 | 7/2007 |
| WO | 2008/060668 A2 | 5/2008 |

OTHER PUBLICATIONS

Denis et al., "System and Method of Controlling Power Delivery to an Electrosurgical Instrument," U.S. Appl. No. 61/669,671, filed Jul. 10, 2012, 59 pages.
Denis et al., "Thermal Surgical Tool," U.S. Appl. No. 61/567,603, filed Dec. 6, 2011, 33 pages.
European Supplementary Search Report, dated Jan. 30, 2015, for European Application No. 12 76 7458, 3 pages.
Extended European Search Report, dated Nov. 10, 2016, for European Application No. 10765134.1-1659, 8 pages.
Extended European Search Report, dated Nov. 28, 2014, for European Application No. 12865504.0-1652, 9 pages.
High Temp Metals, NI 200/201 Technical Data, URL=http://www.hightempmetals.com/techdata/hitempNi200data.php, download date Jul. 16, 2012, 2 pages.
International Preliminary Report on Patentability, dated Apr. 1, 2014, for International Application No. PCT/US2012/055229, 9 pages.
International Preliminary Report on Patentability, dated Jun. 10, 2014, for International Application No. PCT/US2012/068027, 7 pages.
International Preliminary Report on Patentability, dated May 23, 2013, for International Application No. PCT/US2011/050417, 8 pages.
International Preliminary Report on Patentability, dated Nov. 1, 2011, for International Application No. PCT/US2010/031114, 7 pages.
International Preliminary Report on Patentability, dated Nov. 19, 2013, for International Application No. PCT/US2012/038005, 7 pages.
International Preliminary Report on Patentability, dated Oct. 8, 2013, for International Application No. PCT/US2012/032656, 7 pages.
International Preliminary Report on Patentability, dated Oct. 8, 2013, for International Application No. PCT/US2012/032659, 9 pages.
International Preliminary Report on Patentability, dated Oct. 8, 2013, for International Application No. PCT/US2012/032661, 8 pages.
International Search Report and Written Opinion, dated Apr. 12, 2012, for International Application No. PCT/US2011/050417, 12 pages.
International Search Report and Written Opinion, dated Aug. 19, 2013, for International Application No. PCT/US2012/032661, 10 pages.
International Search Report and Written Opinion, dated Feb. 1, 2013, for International Application No. PCT/US2012/055229, 11 pages.
International Search Report and Written Opinion, dated Feb. 15, 2013, for International Application No. PCT/US2012/068027, 8 pages.
International Search Report and Written Opinion, dated Jan. 21, 2011, for International Application No. PCT/US2010/031114, 12 pages.
International Search Report and Written Opinion, dated Nov. 23, 2012, for International Application No. PCT/US2012/032659, 12 pages.
International Search Report and Written Opinion, dated Nov. 23, 2012, for International Application No. PCT/US2012/038005, 9 pages.
International Search Report and Written Opinion, dated Oct. 23, 2012, for International Application No. PCT/US2012/032656, 13 pages.
Japanese Office Action, dated Dec. 11, 2013, for Japanese Application No. 2012-506188, 13 pages. (with English Translation).
Manwaring et al., "Adjustable Ferromagnetic Coated Conductor Thermal Surgical Tool," U.S. Appl. No. 61/170,203, filed Apr. 17, 2009, 36 pages.
Manwaring et al., "Surgical Multi-Mode Tool With Ferromagnetic Coated Conductor for Adjustable Thermal Energy Delivery," U.S. Appl. No. 61/170,207, filed Apr. 17, 2009, 43 pages.
Manwaring et al., "Thermally Adjustable Surgical or Therapeutic Tool and Method of Use," U.S. Appl. No. 61/170,220, filed Apr. 17, 2009, 41 pages.
Metcal, "Soldering, Desoldering and Rework Systems," Product Catalog, 2006, 28 pages.
Smith et al., "A Domain Wall Model for Ferroelectric Hysteresis," *Proceedings of the SPIE Conference on Mathematics and Control in Smart Structures 3667*, Newport Beach, California, USA, Mar. 1, 1999, pp. 150-161.
Visioli, *Practical PID Control*, Springer-Verlag, London, United Kingdom, 2006, pp. 1-18. (20 pages).

\* cited by examiner

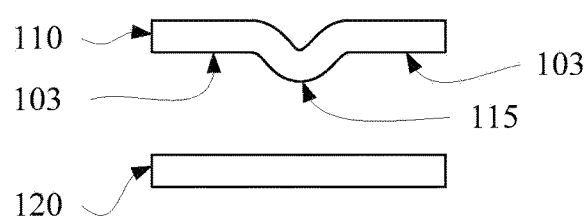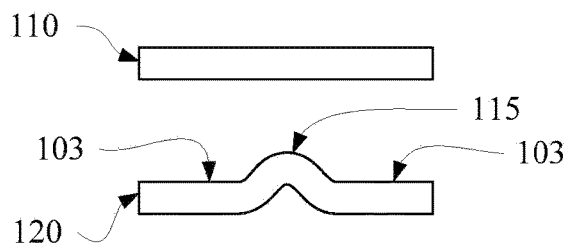
FIG. 8E					FIG. 8F
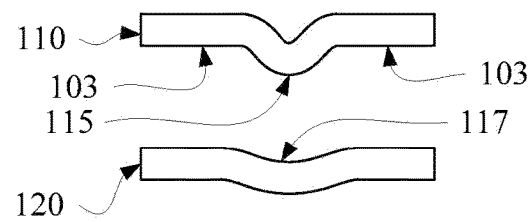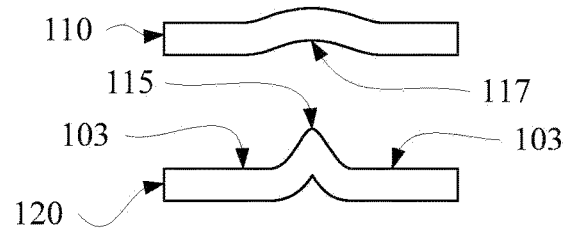
FIG. 8G					FIG. 8H

SEALING AND/OR CUTTING INSTRUMENT

PRIORITY

The present application claims the benefit of U.S. Provisional Patent Application Ser. No. 61/534,047, filed Sep. 13, 2011 and U.S. Provisional Patent Application Ser. No. 61/534,322, filed Sep. 13, 2011, which are incorporated herein by reference in their entirety.

THE FIELD OF THE INVENTION

The present invention relates to surgical instruments. More specifically, the present invention relates to tissue cutting and sealing instruments.

BACKGROUND

Human and animal bodies contain a number of ducts for moving fluids and material, such as blood vessels for carrying blood, the digestive tract for transporting and processing food, reproductive ducts for transporting reproductive fluids and gastric ducts for passing bile and other fluids. (As used herein duct is used broadly to encompass ducts, vessels, tubes and other ducts in a human or animal body. Bodies also include various tissues for performing functions necessary to maintain the body. During surgery, these ducts or tissues may get in the way of the surgical procedure or may need to be cut for a variety of reasons. Additionally, these ducts or tissues may need to be closed and separated. In some cases, these ducts or tissues are the reason or part of the reason for surgery, such as tubal ligation, gall bladder removal, or resecting tissue of an organ, etc. Thus, a surgeon may clamp, block and/or cut ducts or tissue(s) in a variety of situations.

Separating ducts or sealing and cutting tissue can take time and require multiple instruments. Sometimes multiple instruments may be needed for each step during a surgical procedure. In the case of blood, if the surgeon does not adequately clamp, block and cut and tie-off or otherwise seal the blood vessels or other ducts or tissue, blood or other body fluids may leak. This may cause the unfortunate effect of obfuscating the surgical area and create other concerns such as causing blood coagulation and build-up on a surgical instrument. More importantly, the loss of blood can endanger the patient's life. A large bleeder can quickly cause death and even a small bleeder can cause significant injury or death over time. Likewise, the leaking of some body fluids may contaminate the area being operated on.

Cutting and sealing or tying off a blood vessel can be a cumbersome process. If a doctor desires to cut a major vessel, he or she will typically clamp both sides of where the cut is to be made. Once each side is clamped, the incision is made and the ends are either tied off or are sealed to prevent blood loss through the vessel after the incision. In a surgery involving many blood vessels, it can be time consuming and tiring to properly clamp, cut and tie off or seal each vessel. This is particularly so if the surgeon has to cut out or cut through tissue. Thus, there is a need for an instrument that can simply cut tissue, ducts, etc. while preventing leakage from any ducts. Additionally, there is a need for an improved method of clamping, cutting and sealing a duct or tissue in a human or animal body.

Another consideration in sealing and cutting ducts or tissues is ensuring that the sealing and cutting is done generally consistently across the duct or tissue. If the sealing and cutting is done with a scissor-like instrument, more sealing may be applied on one side of the duct or tissue (i.e. the portion closest to the hinge of the surgical instrument) than on the opposing side because more force is applied adjacent the hinge. Thus, it is believed that it would be preferable to have surfaces which are used to seal and cut ducts or tissue to engage the tissue generally parallel to one another, thereby providing a more consistent seal.

SUMMARY OF THE INVENTION

It is an object of the present invention to provide an improved tissue cutting and sealing instrument.

In accordance with the present invention, a surgical instrument is provided with at least one active surface or thermally active element mechanism which has at least one element such that a portion of the active surface or thermally active element mechanism can be heated to a temperature which seals tissue and a portion of the active surface can be heated to a temperature which cuts tissue to thereby allow tissue to be both sealed and cut by the same device.

According to one aspect of the invention, two different energy settings may be sent to a thermally active element to seal and then cut tissue. (As used herein thermally active element and active element may be used interchangeably to reference an element which is heated to treat, e.g. seal or cut tissue). Thus, a physician may attach the instrument to a duct or tissue being cut, seal the duct or tissue to prevent leakage and then cut the duct or tissue between sealed portions to disconnect the two parts of the duct or tissue. Sealing the duct prior to or concurrent with cutting it prevents the contents of the duct or tissue from leaking into a patient's body. This is particularly important when dealing with ducts which carry potentially harmful materials like bile or fecal matter. Thus, in accordance with one aspect of the invention, an instrument is provided which seals and then cuts a duct. This may be accomplished by a single grasp of the duct, with the active element mechanism applying a first, sealing heat and a second, cutting heat to seal and then cut the duct.

In accordance with another aspect of the invention, a single active element may seal and cut the duct with the application of heat of sufficient duration to first seal and then cut the duct.

In accordance with another aspect of the invention, more than one active element may be used. If two elements or more are used, a first element (e.g. an outer element) may seal the duct or tissue first, while a second element (e.g. an inner element) may cut the duct or tissue after it has been sealed, thereby leaving at least a portion of the sealed duct or tissue on either side of the cut.

According to another aspect of the invention, the system may monitor indicators, such as temperature, standing wave ratio ("SWR"), etc. of the active element, or the temperature, electrical impedance, capacitance, conductance, moisture content, etc. in the tissue or contents of the duct, to determine when sealing and/or cutting has been adequately applied.

In accordance with another aspect of the present invention, the elements may be configured for sealing and cutting a duct or other tissue on one side, i.e. cutting a piece of tissue off, or from two or more sides, such as cleaving a piece of tissue along a plane.

According to another aspect of the invention, one or more active elements are disposed on a surgical sealing and cutting instrument which has two treatment surfaces which are disposed generally parallel to each other and remain generally parallel to one another while treatment surfaces are moved into engagement with a duct or tissue to be sealed and/or cut to thereby provide a more consistent seal.

In accordance with another aspect of the present invention, the system may use a parallel surface movement linkage, such as a pantograph linkage to generally equally engage a duct or tissue and to generally equally apply heat and pressure to tissue to ensure adequate and even sealing and cutting has been performed.

These and other aspects of the present invention are realized in a tissue cutting and sealing instrument as shown and described in the following figures and related description.

BRIEF DESCRIPTION OF THE DRAWINGS

Various embodiments of the present invention are shown and described in reference to the numbered drawings wherein:

FIGS. 8E through 8P show end views of alternate configurations of active elements structures which may be used on tips of a surgical sealing and/or cutting instrument according to principles of the present invention;

Figure 1:
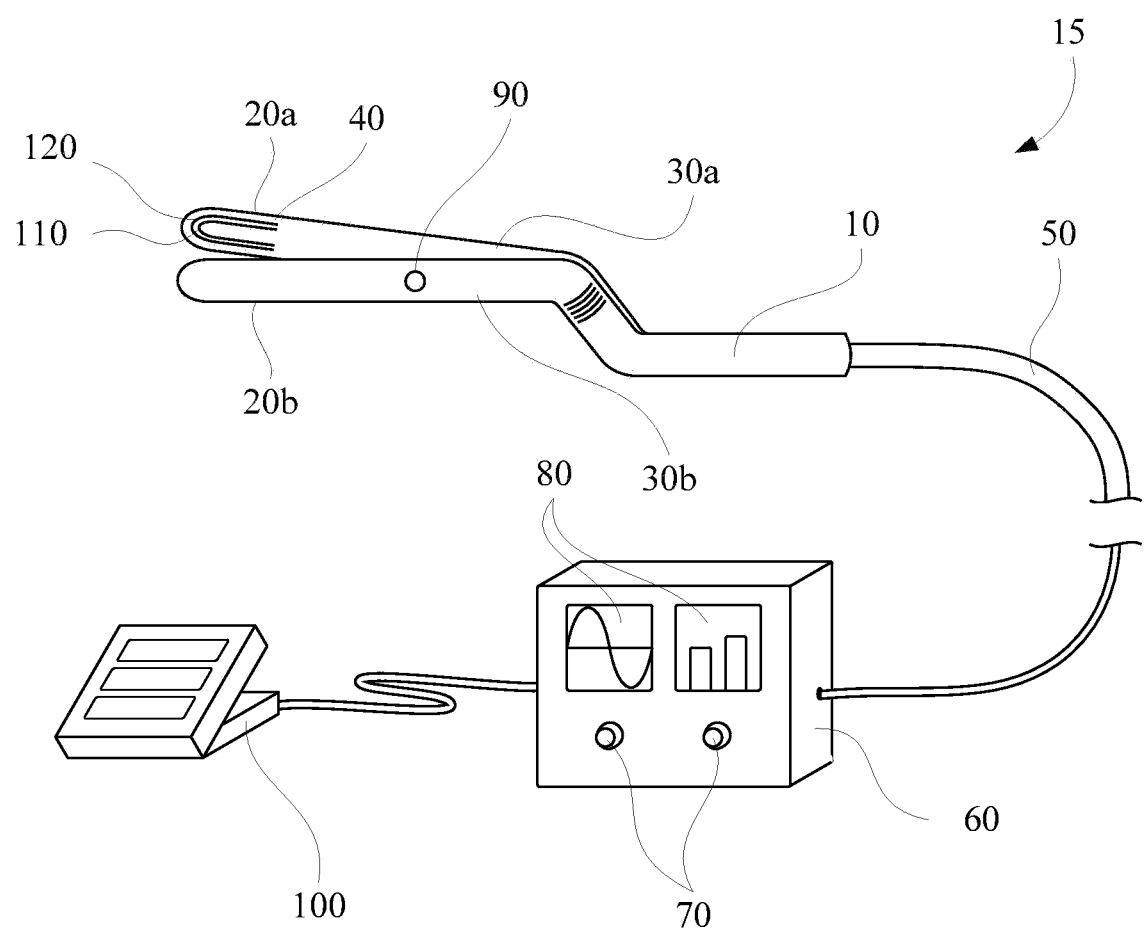
FIG. 1 shows a perspective view of a surgical sealing and/or cutting system.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims. Furthermore, it will be appreciated that the drawings may show aspects of the invention in isolation and the structures in one figure may be used in conjunction with structures shown in other figures.

Tissue sealing may be used to construct a barrier between two or more portions of tissue or duct, or may be used to repair damaged tissue. In many cases, the tissue or duct may provide a pathway for delivery of material, such as eggs in a fallopian tube or blood in a blood vessel. A barrier may thus prevent functional operation, in the case of the fallopian tube, or even prevent leakage, such as in the case of the blood vessel. The barrier may also prevent contamination, by closing a potential entrance or exit for contaminants. In some cases, it may be desirable to cut the tissue apart after sealing. Each portion of separated tissue may retain some of the seal. Thus, the tissue seal may act as a barrier to prevent contents of the tissue exiting and/or other contaminants entering the cut tissue. Likewise, tissue having an open wound or otherwise needing to be sealed off can be sealed to close the wound and prevent entry of contaminants or to prevent exit of material from the tissue.

For example, tissue sealing and cutting may be used for tubal ligation. A fallopian tube may be sealed and then cut. By sealing the fallopian tube, eggs may be prevented from navigating the fallopian tubes and entering the uterus. However, to ensure that the flow of an egg into the uterus is not possible, the sealed tube is ligated as well. Similarly, blood vessels may be sealed to stop blood flow prior to being cut to prevent bleeding during and immediately after the cut. As will be explained below, ferromagnetic covered conductors may provide advantages in sealing and cutting ducts and other tissues, including reduced cost, simplicity of operation and increased effectiveness in tissue sealing and cutting instruments.

In FIGS. 1 to 19, there are shown tissue sealing and cutting instruments in accordance with one aspect of the present invention. In FIGS. 20 to 28, there are shown surgical instruments in accordance with another aspect of the present invention, and which may be used in conjunction with the tissue sealing and cutting instruments discussed in FIGS. 1 to 19. Parallel surface movement may include a ferromagnetic covered conductor based tissue sealing and cutting instrument described in FIGS. 1 to 19, along with other sealing and cutting technologies. In FIG. 29, a chart of estimated temperature correlation to tissue effects is shown.

Turning now specifically to FIG. 1, a perspective view of a handheld sealing and cutting instrument 10 and system 15 is shown. Many surgical procedures require cutting or ligating ducts, such as blood vessels, or other vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing a surgical sealing and/or cutting instrument 10, a surgeon can cauterize, coagulate/desiccate and/or simply reduce or slow bleeding.

For treating larger vessels, a surgeon may opt to seal the tissue or vessel. Tissue sealing is fundamentally different than simply coagulating or cauterizing vessels. For the purposes herein, "coagulation" is defined as a process of desiccating tissue wherein the tissue cells are ruptured and dried. "Duct sealing", "vessel sealing" or "tissue sealing" is defined as the process of liquefying the collagen in the duct, vessel, tissue, etc. so that it reforms into a fused mass with limited demarcation between adjacent tissue structures. In order to effectively seal larger ducts (or tissue) two predominant parameters must be accurately controlled—the pressure applied to the duct or tissue and the amount of heat which is conducted from the tip 20A and/or tip 20B to the duct or tissue.

It will be appreciated that the surgical sealing and cutting instrument 10 varies from many prior art electrosurgical tools in that in the instrument of the present invention heat is generated directly in an active element 110 located on tip 20A and/or 20B. This is in contrast to many electrosurgical instruments, such as bipolar or monopolar instruments, which use one or more probes to direct electrical current into tissue where the resistance to the electrical current generates heat in the tissue rather than at a thermal element. In other words, a thermal instrument generates heat and applies the heat to the tissue, while monopolar and bipolar devices pass electricity into the tissue which results in heat being developed in the tissue.

In use the sealing and/or cutting instrument 10 has tips 20A, 20B which may be placed around or on opposing sides of a duct or tissue to be sealed. The tips 20A and 20B may be placed at the end of arms 30A, 30B which are held in a user's hand. A user may squeeze the arms 30A, 30B of the instrument together causing the tips 20A, 20B to provide pressure on the duct or tissue. Electrical energy may then be directed to an active element 120 on the active surface 40 of tip 20A and/or 20B to heat the thermally active element 120. (It will be appreciated that the active element could be applied hot to the duct, or could by applied and then heated). The heat generated in the active element is applied to the duct or tissue to cause the duct or tissue to seal. In accordance with one aspect of the invention, a second energy level may be applied to the active element 110 (or a separate active element) to heat the active element 110 to a second temperature that is sufficient to cut the duct or tissue apart. This may be accomplished using one element 110 or by separate elements 110, 120. Power may be received by the instrument 10 through a cable 50.

Alternatively, electrical energy may be delivered to one or more active elements, such as active elements 110, 120, substantially simultaneously to seal and cut the duct or tissue. Under such circumstances, active element 110 may be configured to provide a higher thermal density as compared to the thermal density provided by active element 120. (As used herein "thermal density" means the rate at which thermal energy is conducted into a duct or tissue.) Thus, the process of sealing and cutting a duct or tissue can be initiated substantially simultaneously, rather than sequentially, to reduce the amount of time it would take a surgeon to seal and cut the duct or tissue. As explained in more detail below, it will be appreciated that a single active element having a surface may be shaped to provide a higher thermal density to the duct or tissue at a particular location along the surface. Thus, a single active element may be used to both seal and cut a duct or tissue according to principles of the present invention.

According to one aspect of the invention, the active element 110 (and/or active element 120) may be formed by a conductor having a ferromagnetic coating to form a thermally active element. As used herein, the term "ferromagnetic," "ferromagnet," and "ferromagnetism" refers to any ferromagnetic-like material that is capable of producing heat via magnetic induction, including but not limited to ferromagnets and ferrimagnets. It is not intended that such materials must be heated exclusively by magnetic induction unless otherwise indicated and such may acquire heat from resistive heating, eddy currents, etc., in addition to magnetic induction. Power, such as a radio frequency (RF) waveform, may be provided to the conductor. The RF energy may travel along the conductor's surface in a manner known as the "skin effect". The current density is generally greatest at the surface and decreases in magnitude further into the material where the electric field approaches zero. The depth at which the skin effect current is reduced to about 37 percent of its surface value is referred to as the skin depth and is a function of the electrical resistivity, the magnetic permeability of the material conducting the current, and the frequency of the applied alternating RF current.

The alternating RF current in the conductor's surface produces an alternating magnetic field, which may excite the domains in the ferromagnetic portion 65. As the domains realign with each oscillation of the current, hysteresis losses in the coating may cause inductive heating. Heating of the ferromagnetic portion 65 due to hysteresis loss ceases above the Curie point because the material loses its magnetic properties.

According to one aspect of the invention, the ferromagnetic coating may have a thickness of approximately 4 to 5 skin depths. As the power passes through the conductor, heat is produced in the ferromagnetic material. For the purposes herein, the heat produced in the ferromagnetic material may be referred to as "ferromagnetic heat" or "ferromagnetic heating" and includes heat produced by magnetic induction or related mechanisms caused by delivering electrical energy from a power source to a ferromagnetic coated conductor in a closed circuit. As explained above, heat may also be generated in the ferromagnetic material due to resistive heating, eddy currents, etc., however, ferromagnetic heat and ferromagnetic heating excludes heat generated by an electrosurgical element that is used to direct electrical energy into tissue to cause heating of the tissue directly, such as a bipolar or monopolar instrument. Thus, it is anticipated that the principle source of heat will be current passing through the thermally active element rather than current passing through tissue adjacent thereto.

When the ferromagnetic coating is thin relative to the conductor, the ferromagnetic coating can quickly heat to temperatures which will seal and/or cut tissue, and then rapidly cool to a temperature where the ferromagnetic coating will not even burn the skin within a very short time period. For example, a tungsten conductor having a diameter of about 0.375 mm and a ferromagnetic coating of a Nickel Iron alloy (such as NIRON™ available from Enthone, Inc. of West Haven, Conn.) about the tungsten conductor about 0.0375 mm thick can be used as the element. Multiple different frequencies can be used, including frequencies from 5 megahertz to 24 gigahertz. Further, a ferromagnetic covered conductor may be comprised of a ferromagnetic material generally surrounding an electrical conductor (either touching or not touching the conductor), and which produces heat when electrical energy is supplied to the conductor. A more detailed discussion of powering ferromagnetic coated/covered conductors to generate heat sufficient to seal and/or cut through tissue is described in more detail in U.S. Publication No. US-2010-0268207-A1 and US-2010-0268210-A1, which are expressly incorporated herein in their entirety. It will be appreciated that improved heat may be obtained by a ferromagnetic coating which completely circumscribes the conductor along the portion desired to be heated.

Energy may be provided by a power supply 60 through the cable 50 to the handheld sealing and/or cutting instrument 10. The energy may be, for example, an oscillating current, such as an alternating RF signal. The power supply may include settings 70, displays 80 and one or more cables, such as cable 50. The current power setting may be controlled by a switch 90 on the forceps or foot pedal 100 connected to the power supply by a cable or through wireless communication. Current may be passed from the power supply 60, through the cable 50, through the instrument 10 and along the conductor through the ferromagnetic portion and back to the power supply with the vast majority of the current staying in the conductive pathway of the tool rather than being transmitted through tissue.

The handheld sealing and/or cutting instrument 10 may have one or more active surfaces 40. In one embodiment, the active surface is only on tip 20A. In another embodiment, an active surface may be on both tips 20A and 20B. For example, tip 20B may be a mirror image of tip 20A. A single active surface 40 may be desirable and cost efficient for smaller ducts or tissues to be sealed. Multiple active surfaces may be desirable for work on larger tissues, as the heat may be more consistently presented to the tissue.

The active surface 40 may include one or more active element 110, 120. The active element may be embedded in a layer of material at the active surface 40 or may extend outwardly from or located adjacent to the active surface 40 so that it is positioned away from the surface of the forceps tips 20A, 20B. Thus, the elements 110, 120 may be configured to seal and/or cut when the surface 40 touches tissue, or may seal or cut prior to the surface 40 engaging the tissue. Moreover, the element(s) 110, 120 may themselves be the surface which engages the tissue.

It will be appreciated that the active element(s) 110, 120 on each of the tips 20A and 20B may be activated at the same time, or one or both may be operated separately. Thus, for example, if a surgeon needs to seal a small vessel or other duct, he or she may activate sealing tip 20A or 20B and then activate both when encountering a larger vessel or duct.

Figure 2:
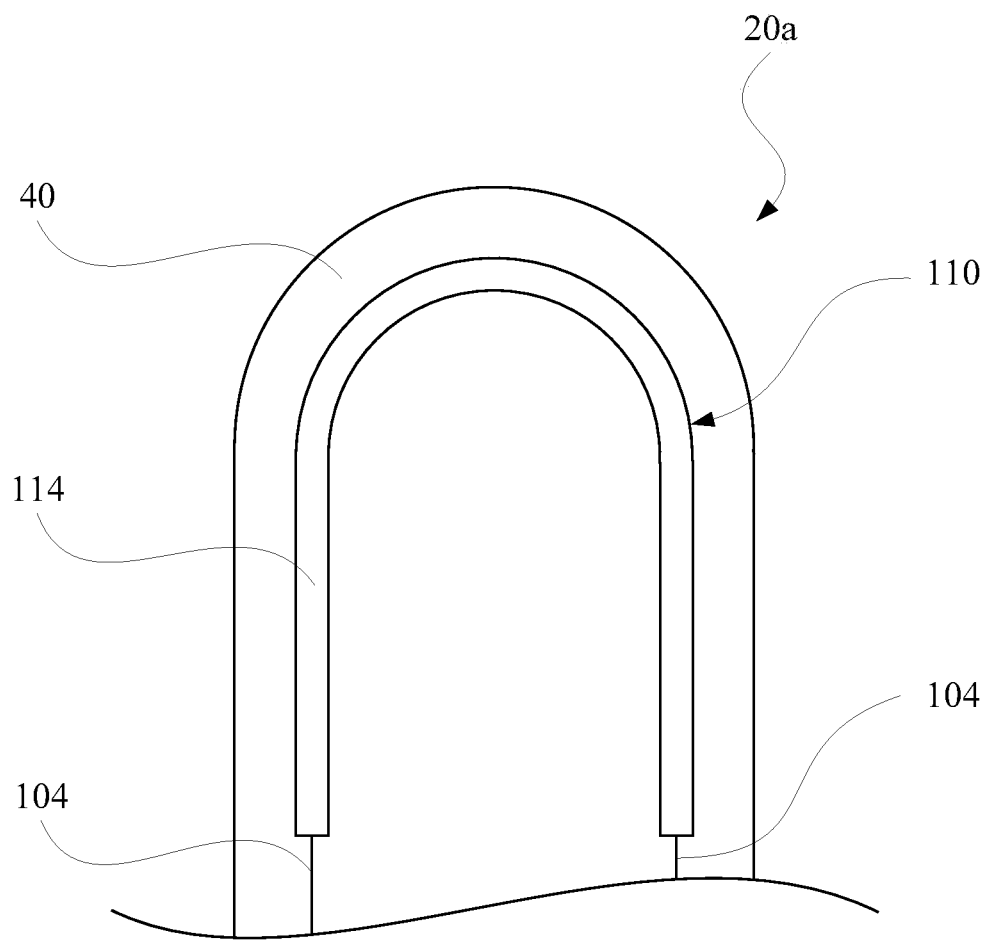
FIG. 2 shows a close-up, fragmented view of a single element tip of a surgical sealing and/or cutting instrument.

Turning now to FIG. 2, a close-up view of a single element tip, such as tip 20A, of a handheld sealing instrument is shown. In one embodiment, tip 20A may include an active surface 40 with a single active element 110, which may be loop or shaped as an elongated arch, i.e. an arch with two arms extending from the curved portion. The active element 110 may be a material which will heat sufficiently to seal and/or cut human or animal ducts or tissue. The active element 110 may be, for example, a conductor 104 forming a closed circuit with a power source and having a ferromagnetic coating 114 disposed on the conductor. The single active element 110 may be able to function with at least two energy settings: a setting for sealing tissue together and a setting for cutting through tissue.

For example, a surgeon may use pressure to apply the active surface 40 to a blood vessel or other duct. This may include the blood vessel being disposed across the arms of the active element extending from the art. The surgeon may then control power delivered to the ferromagnetic covered conductor forming the active element 110 by activating a first power setting causing the blood vessel or other duct to seal or weld closed, at two locations depending on the distance between the arms. If needed, the surgeon may repeat the sealing on adjacent blood vessel tissue to provide a wider seal. The surgeon may then place the active surface 40 in the middle of the sealed tissue (or leave the active surface 40 where it is, if the surgeon did not move it). The surgeon may activate a second power setting to cause a portion of the sealed blood vessel or other duct to be cut with heat generated in the ferromagnetic coating of the active element 110. Thus the blood vessel or other duct may be sealed closed from contamination and/or leakage while being separated into two parts (or being sealed before being cut and then having the open end cut off distal to the seal). It will be appreciated that there are several ways for controlling whether sealing or cutting heat is applied, such as by regulating the duty cycle to control the amount of heat being generated in the ferromagnetic coating 114.

Figure 3:
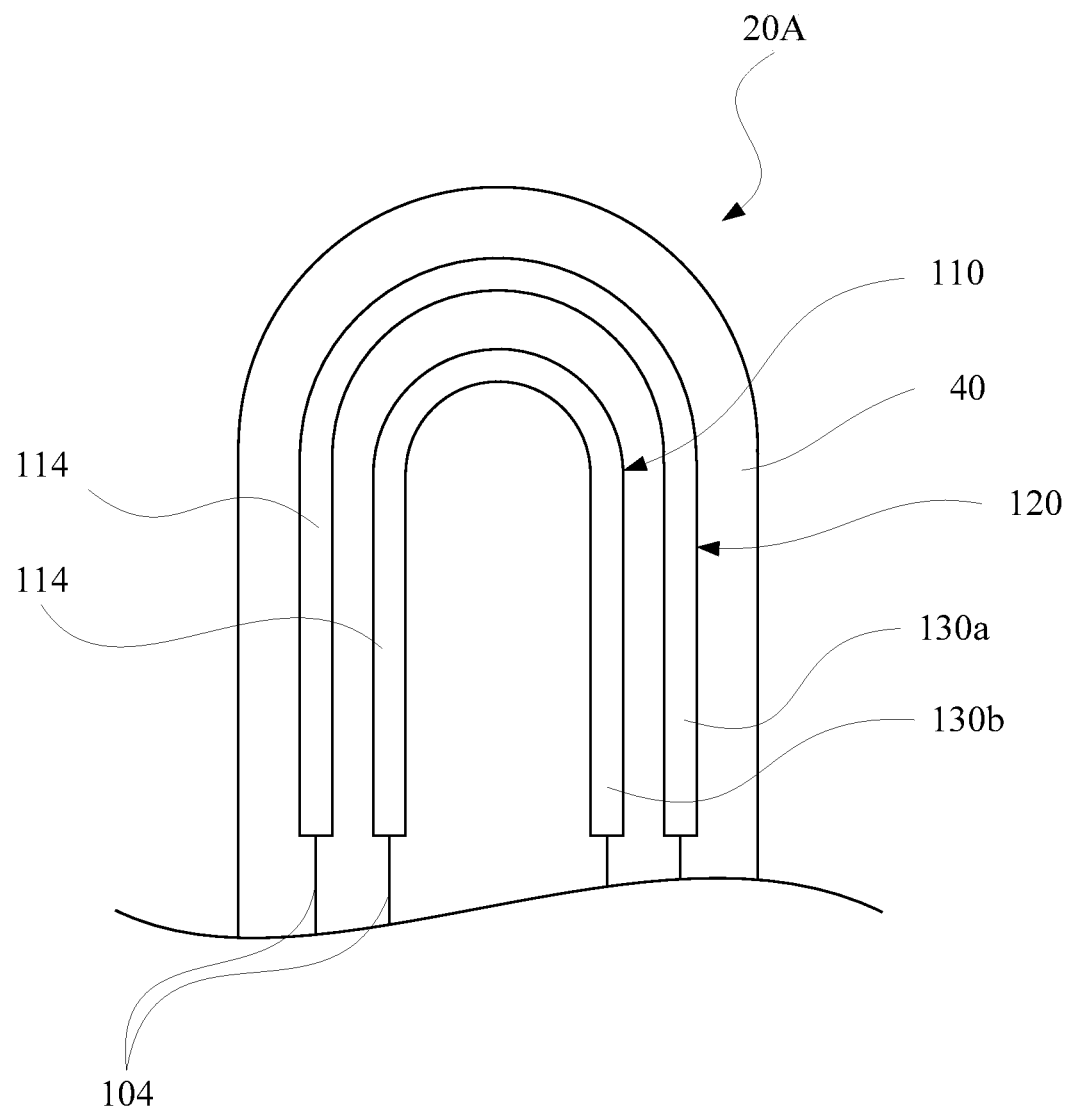
FIG. 3 shows a close-up, fragmented view of a double element tip of a surgical sealing instrument.

Turning now to FIG. 3, a side view of a double active element tip of a handheld sealing instrument is shown. In one embodiment, a tip 20A may include an active surface 40 with two active elements 110, 120 which are controlled together or separately, or by two active sub-elements 130A, 130B (i.e. two portions of a common element) which may be controlled together, such as a pair of ferromagnetic covered conductors. For ease of reference, the conductors may be referred to as separate elements 110, 120 regardless of whether a single element with two parts or two separate elements etc., is used, unless specifically designated as one or the other. Examples of sub-elements, as the term is used herein, may include an active element comprising a conductor having a plurality of spaced apart ferromagnetic coatings thereon, an active element comprising a conductor having a first coating of a first ferromagnetic material and a second coating of a second ferromagnetic material different than the first ferromagnetic material, etc. It will be further appreciated that while two elements or sub-elements are shown, an active surface 40 having a larger number of elements or sub-elements may be used for a variety of purposes.

The active element(s) 110, 120 may use a separate power setting for each sub-element 130A, 130B or conductor 104. The outer sub-element 130A or element 120 may be configured for a sealing temperature range, such as a temperature range sufficient to heat the tissue to about 58° C. to 200° C. or more preferably 58° C. to 62° C. The inner element 130B or element 110 may be configured for a cutting temperature, such as a temperature range sufficient to heat the tissue to about 200° C. to 500° C., or more preferably 200° C. to 400° C. By using an outer sub-element 130A or element 120 to seal and an inner sub-element 130B or element 110 to cut, the inner element/sub-element may avoid cutting the sealed portions of a duct or vessel by cutting in between the seals. (It will be appreciated that inner and outer are used for convenience only and are not intended to limit the geometry of the active elements 110, 120.) When a sealing element and a cutting element are used, the sealing element may be above, below, on either side or any other position relative to the cutting element which is desired by the surgeon. The result of a duct being disposed across the active elements 110, 120 will be two seals and two cuts between the seals, thus clearly terminating flow through the duct and sealing the duct adjacent the cut which minimizes the risk of accidentally cutting through the seal.

Elements 110 and 120 are shown as having a generally loop or curve-shape end with arms extending therefrom. Additionally, the thermally active elements 110, 120 are shown as being generally parallel to one another. This allows the element 100, 120 to be placed on a duct with the length of the loop generally perpendicular to the duct with the outer element 120 sealing the duct and the inner element 110 cutting the duct to remove a small segment and leave sealed segments on either site of the cuts. It will also be appreciated that in certain surgeries, different configurations may be desirable depending on the orientation of the ducts which are to be sealed. Any such geometries are intended to be covered by the claims unless specifically limited therein.)

For example, a surgeon may use pressure to apply the active surface 40 to a blood vessel. The surgeon may then cause the outer element 120, which may be a ferromagnetic covered or coated conductor, to receive a first power setting causing the blood vessel to seal or weld closed. The surgeon may then activate a second power setting to the inner element 110, which may be a ferromagnetic covered or coated conductor, causing an inner portion of the sealed blood vessel to be cut out of the blood vessel. The same procedure may be used with other ducts as well.

It will be appreciated that the active surface may be used both to cut an intact duct, for example to both seal and cut a fallopian tube, or to seal and then cut off the end of a duct which has already been cut, such as sealing off a severed blood vessel and then cutting off the excess vessel beyond the seal, if necessary. Thus the blood vessel may be sealed closed from contamination and/or leakage while being separated into two parts or cleaned up after being cut, if necessary.

Figure 4:
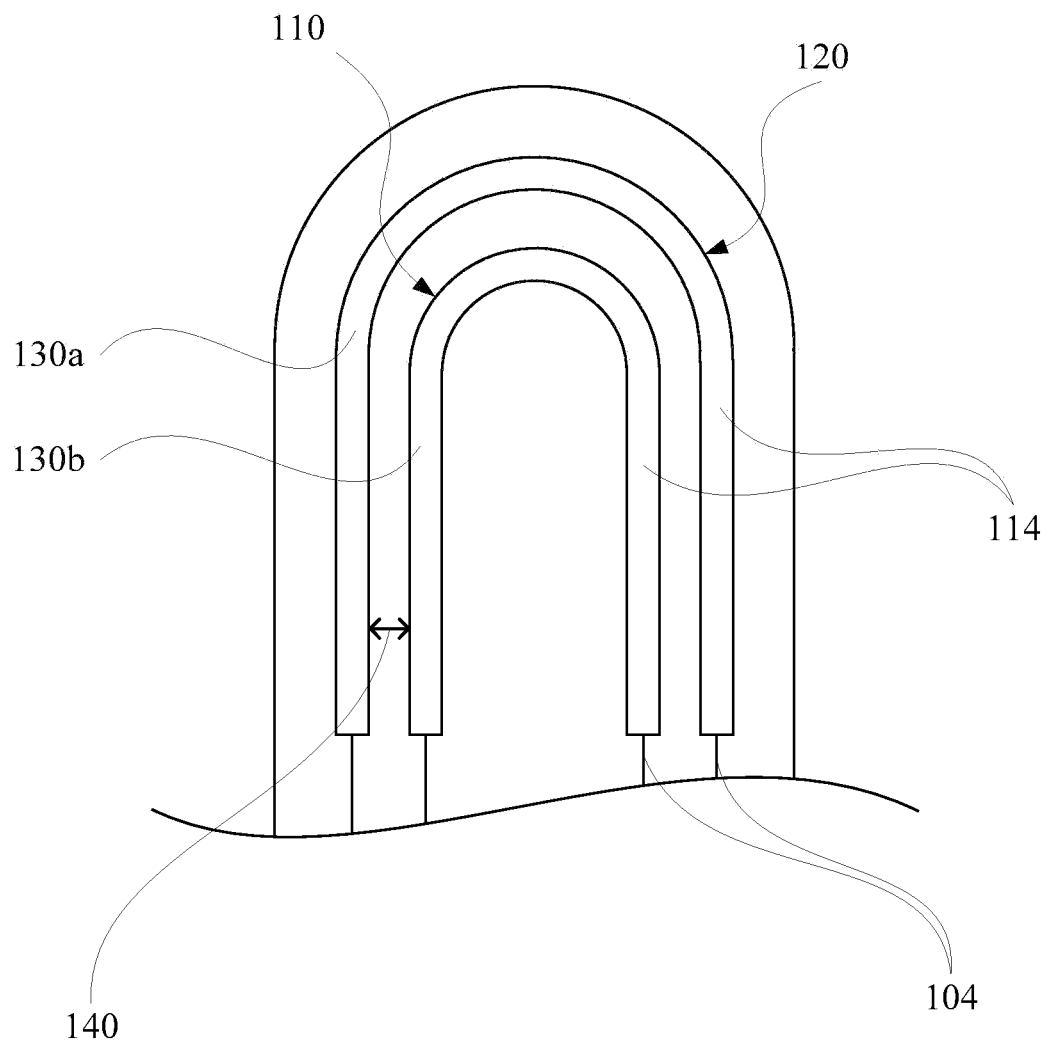
FIG. 4 shows a close-up, fragmented view of a surgical sealing instrument showing a sealing barrier.

Turning now to FIG. 4, a side view of a sealing barrier distance 140 of a handheld sealing instrument is shown. The sealing barrier distance 140 between the outer sub-element 130A (or element 120) and inner sub-element 130B (or element 110) may determine the amount of sealed tissue remaining on each side of a cut performed by the inner sub-element 130B. Depending on the tissue, the sealing barrier distance 140 may be adjusted. This may be done by selecting forceps 10 (FIG. 1) with tips 20A or 20b having sub-elements 130A and 130B at a desired distance, by having one of the sub-elements be adjustable, or by having forceps with one tip 20A having a first distance between the sub-elements, and the other tip 20B having a different distance between the sub-elements so that the surgeon can choose which tip to use.

According to one aspect of the invention, the distance may be adjusted as the outer and/or inner active elements may be malleable. A tip linkage may move the outer and/or inner active elements to increase or decrease distance between the outer and inner active elements.

Active elements may include multiple different technologies. In some cases, two technologies may be combined. For example, a bipolar element may be used as the outer sealing element, while a ferromagnetic covered conductor may be used to cut the tissue as an inner element, or vice versa. Ferromagnetic covered conductors may be desirable for many applications because of their ability to quickly heat and cool, as well as the small amount of tissue damage beyond the point of contact. In one embodiment the ferromagnetic coating circumscribes the conductor to facilitate inductive heating.

The system may also incorporate sensors to aid in the determination of appropriate sealing times and cutting application times. The system may monitor the temperature, standing wave ratio ("SWR"), etc. of each active element, or the temperature, conductivity, moisture content, or impedance or some combination thereof, of the tissue. In one embodiment, the system automatically seals and then cuts the tissue when the surgeon applies the instrument to tissue and activates the instrument. This could be done, for example, by monitoring the moisture content of the tissue. During the sealing step, the tissue will lose moisture content to a point, at which cutting will begin. Thus, moisture content passing beyond a desired threshold can be used to raise an indicia that sealing is complete and cutting has or will begin.

Figure 17:
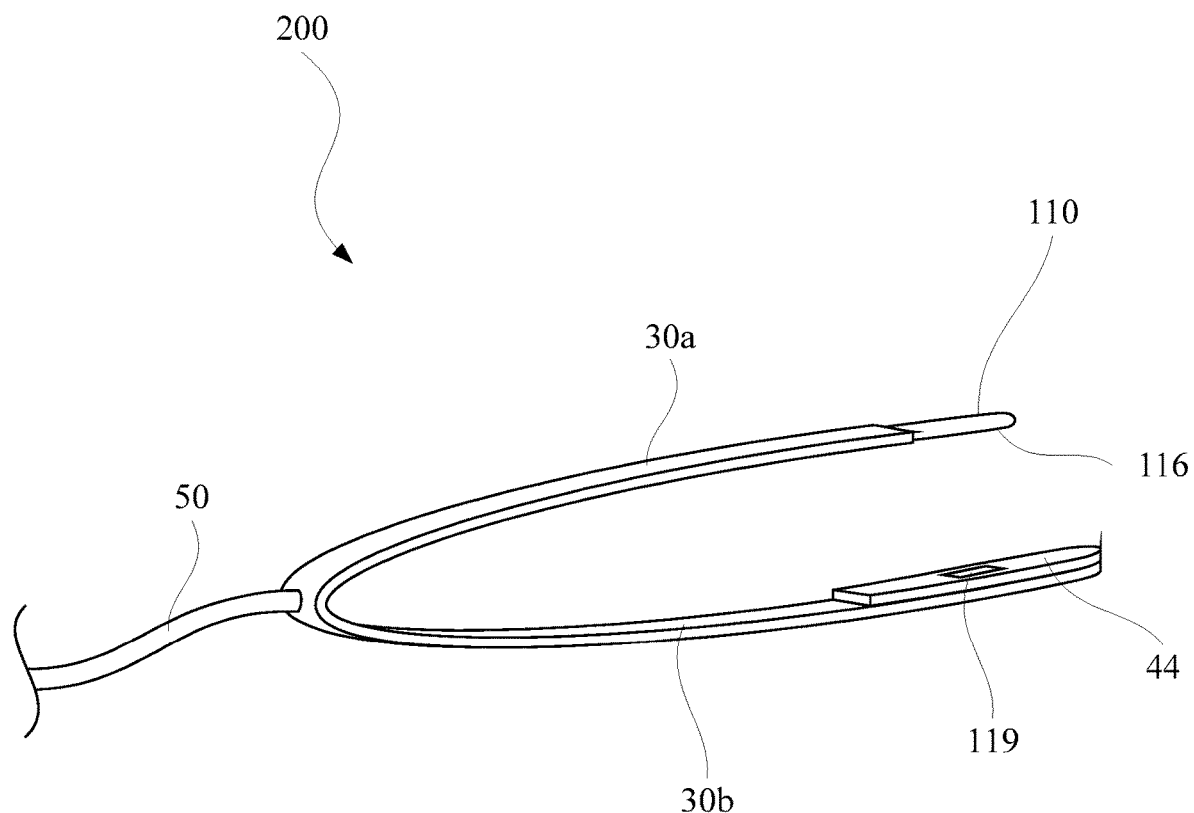
FIG. 17 shows a perspective view of another surgical instrument having cooperating elements

Likewise, the system may monitor temperature over time (using, for example, a sensor as shown in FIG. 17) and determine when appropriate sealing has been completed before the cut energy is applied. This can be done by monitoring the temperature of the element which will tend to stay near a fixed temperature until sealing is complete, and then suddenly rise as it cuts. Alternatively, the system may monitor may monitor the temperature, electrical properties, or some other characteristic, of the tissue or duct, using a sensor (see e.g. FIG. 17) located on one or both of the tips 20A and 20B. Thus, the temperature, electrical properties, etc. of the tissue or duct can be monitored across from, or adjacent to, the sealing and/or cutting elements. According to one aspect of the invention, a light or sound may be emitted from the instrument or power supply to notify the surgeon when a phase appears to be completed. Thus, the surgeon may listen for a first sound or see a first light to know that a sealing phase is completed. The surgeon may then activate the cutting phase and await a second light or sound to know that the cutting phase is completed and the instrument may be removed, or the instrument may automatically perform each step and provide notification when each is complete.

During a procedure, power delivery to the sealing instrument 10 may be controlled by varying the amplitude, frequency or duty cycle of the alternating current waveform, or alteration of the circuit to affect the standing wave driving the ferromagnetic coated conductor.

Figure 5:
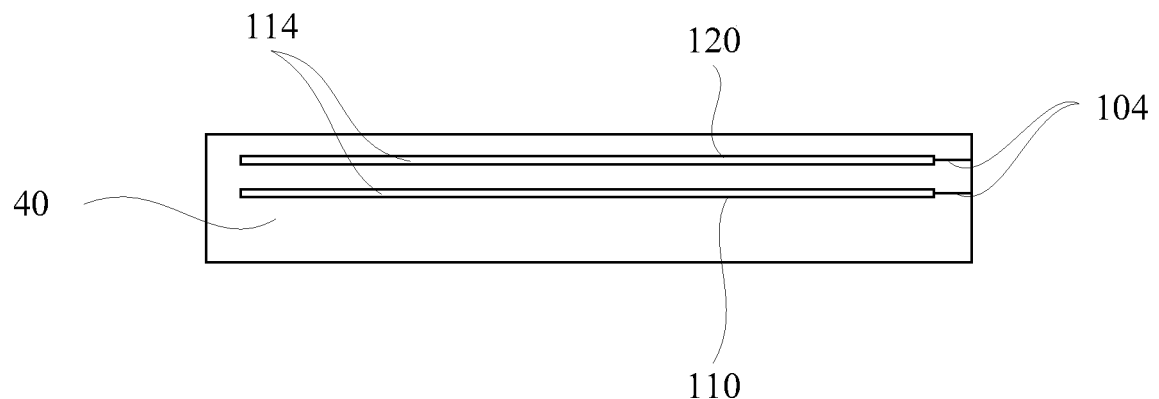
FIG. 5 shows a close-up, fragmented view of a surgical sealing instrument with two sealing elements in an alternate configuration.

Turning now to FIG. 5, there is shown an alternate arrangement of an active surface 40. In FIGS. 1-4, the active element(s) 110, 120 were generally U-shaped as may be beneficial for sealing and cutting out a portion of a duct. There are situations, however, where it is desirable to cut off or cut out a portion of tissue or a duct which involves sealing and cutting tissue over an elongate area. Thus, rather than using an active surface 40 having U-shaped active element(s) 110, 120, FIG. 5 shows active elements which may be generally linear and generally parallel and which may be used in a manner somewhat analogous to use of a pair of scissors. (As explained in more detail below, the active element(s) 110, 120 shown in FIGS. 5-7 may be formed from a flattened conductor 104 covered by a ferromagnetic coating 114.) If desired one or both conductors 104 and/or the coatings may be flattened.

As shown in FIG. 5, one element 120 may be used for sealing, while another element 110 may be used for cutting. Thus, a surgeon or other user would engage the tissue and activate the sealing element 120 and the cutting element 110. This may be done simultaneously or sequentially depending on the time necessary for the sealing element 120 to adequately seal off fluid flow through the tissue. By advancing the active surface 40 along the tissue, and activating the active elements 110 and 120, the tissue on the side of element 110 opposite element 120 would be cut off.

While reference is made to an active surface 40, it will be appreciated that the active element may be in the active surface or extend outwardly from the active surface depending on the intended use and the desires of the user. Thus, it will be appreciated that active surface 40 itself need not seal or cut tissue.

Figure 6:
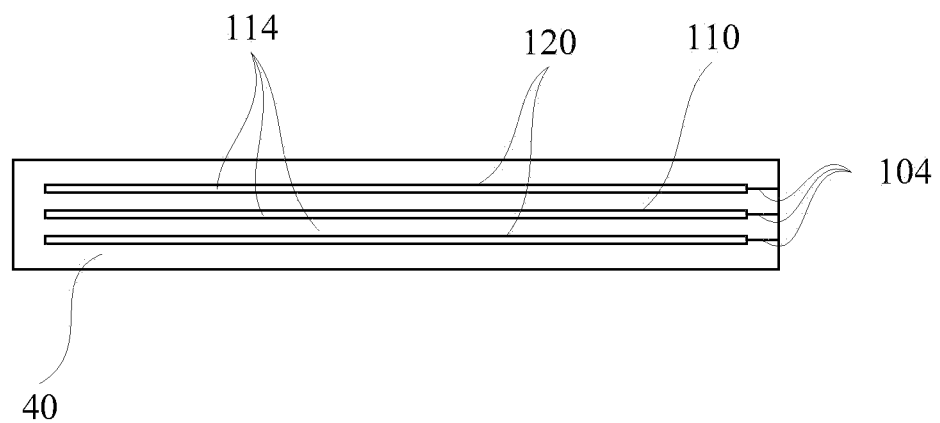
FIG. 6 shows a close-up, fragmented view of a surgical sealing instrument with three elements in a configuration similar to that of FIG. 5.

Turning to FIG. 6, there is shown an alternate configuration of an active surface 40. The active surface 40 may include two sealing active elements 120 and a cutting active element 110 disposed therebetween. (As used herein, a sealing active element is a thermally active element which is heated to seal tissue and a cutting active element is a thermally active element heated sufficiently to cut tissue. It will be appreciated that one element could function as both depending on how it is controlled.)

In use the active surface 40 may be placed along a tissue to be cut. The sealing active elements 120 may be used to seal the tissue on either side of the cutting active element 110 and the cutting active element used to cut the tissue to ensure that flow between opposing sides does not continue. Thus, for example, if flow through a duct needed to be prevented, the duct will be sealed on either side of the cut, thereby ensuring both sealing and cutting of the duct.

Figure 7:
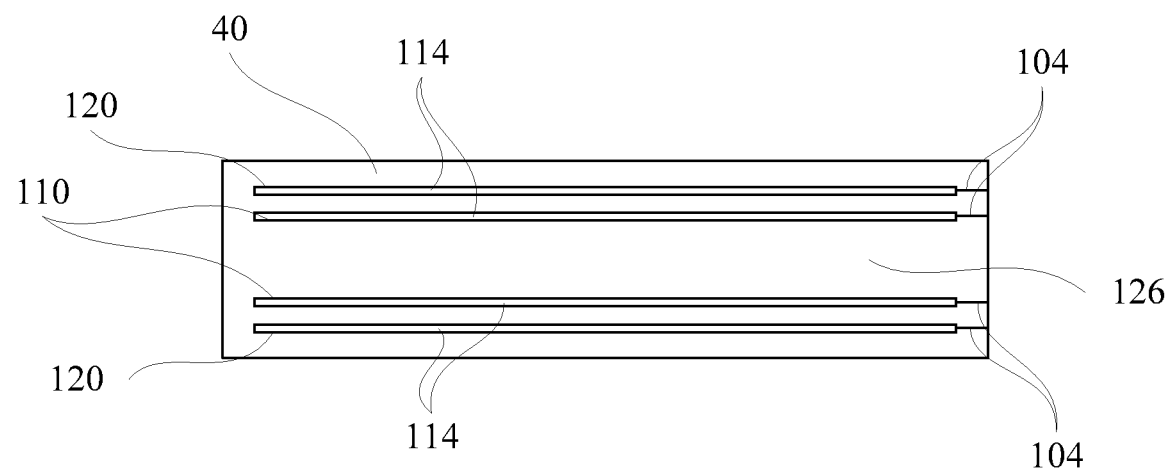
FIG. 7 shows a close-up, fragmented view of the active surface of a surgical sealing instrument with four elements in a configuration similar to that of FIG. 6.

Turning now to FIG. 7, there is shown yet another configuration of an active surface 40. The active surface 40 may include two sealing active elements 120 which are spaced apart and two cutting active elements 110 which are spaced apart a desired distance 126. In use the active surface can be placed on a tissue or duct to be cut (with the length generally perpendicular to the length of the duct) and the active elements 110, 120 energized to seal and cut the tissue or duct. In addition to sealing and/or cutting the tissue or duct, the arrangement of the cutting active elements 110 will cut out a strip of the tissue or duct. This may be desirable when the active elements are being used to remove a diseased portion of tissue, or where is it desirable to remove a segment of a duct to ensure that flow therethrough has been terminated. For example, in tubal ligation, it is often required to affirmatively remove a section of the fallopian tube to ensure that there is no risk of pregnancy in the future. With the active surface of FIG. 7, both sides of the cut will be sealed and a segment between the cuts can be removed for adequate reassurance that flow through the fallopian tube is no longer possible.

Figure 8A:
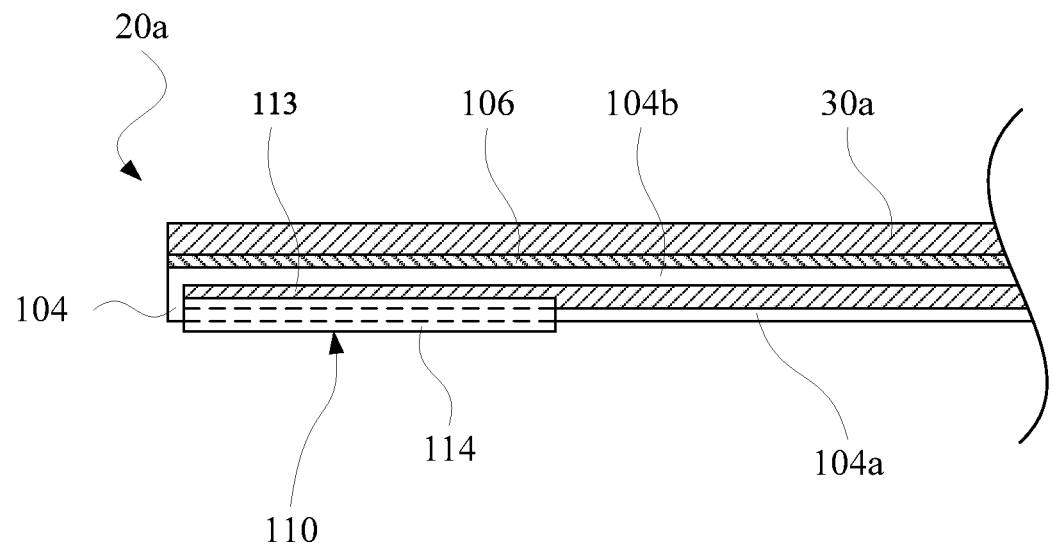
FIG. 8A shows a fragmented, cross-sectional view of an alternate configuration for the tip of a surgical sealing instrument according to principles of the present invention.
Figure 8B:
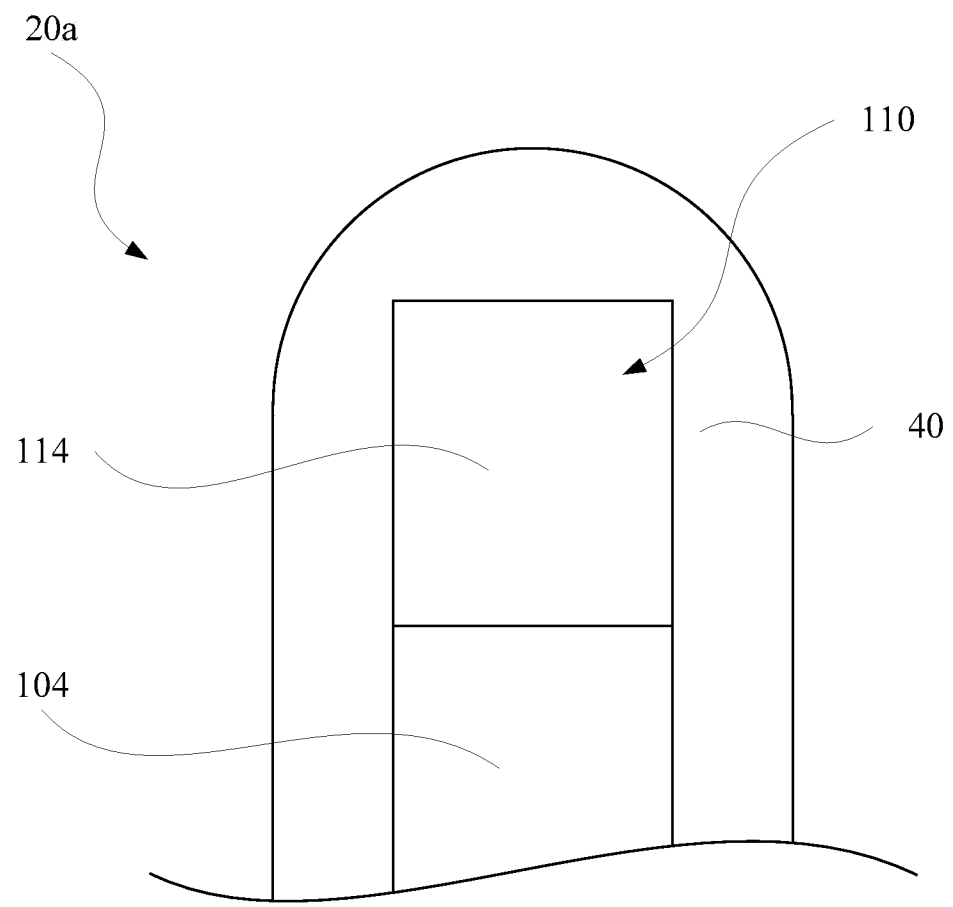
FIG. 8B shows a close close-up, fragmented view of the active surface of the surgical sealing instrument shown in FIG. 8A.

Turning now to FIGS. 8A and 8B, there is shown an alternate configuration for the tip, generally indicated at 20A, of a surgical sealing instrument according to principles of the present invention. Similar to the tips described above, the tip 20A may include a thermally active element 110 comprised of a conductor 104 having a ferromagnetic coating 114 disposed thereabout to form a ferromagnetic heating region. The active element 110, however, may form a generally flat, planar surface. The generally planar surface of the active element may be formed by flattening a section of a conductor wire 104 and plating a coating of ferromagnetic material 114 on the flattened conductor 104 such that the ferromagnetic coating 114 substantially covers the entire outer surface of a length of the flattened conductor 104. (The coating 114 may extend completely around the conductor 104 if desired). The flattened conductor 104 may form a closed circuit with a power source directly or via intervening conductors such that applying electrical energy across the flattened conductor causes substantial uniform ferromagnetic heating along the ferromagnetic region of the active element 110.

The flattened conductor may extend along an arm 30A of a sealing and/or cutting instrument of the present invention, such that electrical energy supplied from a power source travels towards the ferromagnetic material 114 through section 104a of the conductor 104, away from the ferromagnetic material 114 through section 104b of the conductor 104, and back to the power supply. (It will be appreciated that, alternatively, electrical energy could travel towards the ferromagnetic material 114 through section 104b and away from the conductor through section 104a). Arm 30A may include a thermally and/or electrically isolating material 106 to substantially prevent transfer of heat and/or electrical current to the arm 30A of the surgical sealing and/or cutting instrument. Additionally, an electrically isolating material 113 may be disposed between sections 104a, 104b of the conductor 104 to prevent current from bypassing the ferromagnetic material.

As will be appreciated, the active element 110 shown in FIGS. 8A and 8B will have a larger surface area for contacting a duct or tissue to be sealed and/or cut. By applying heat to a duct or tissue using an active element 110 with a larger surface area a better seal may be created along the duct or tissue.

Figure 8C:
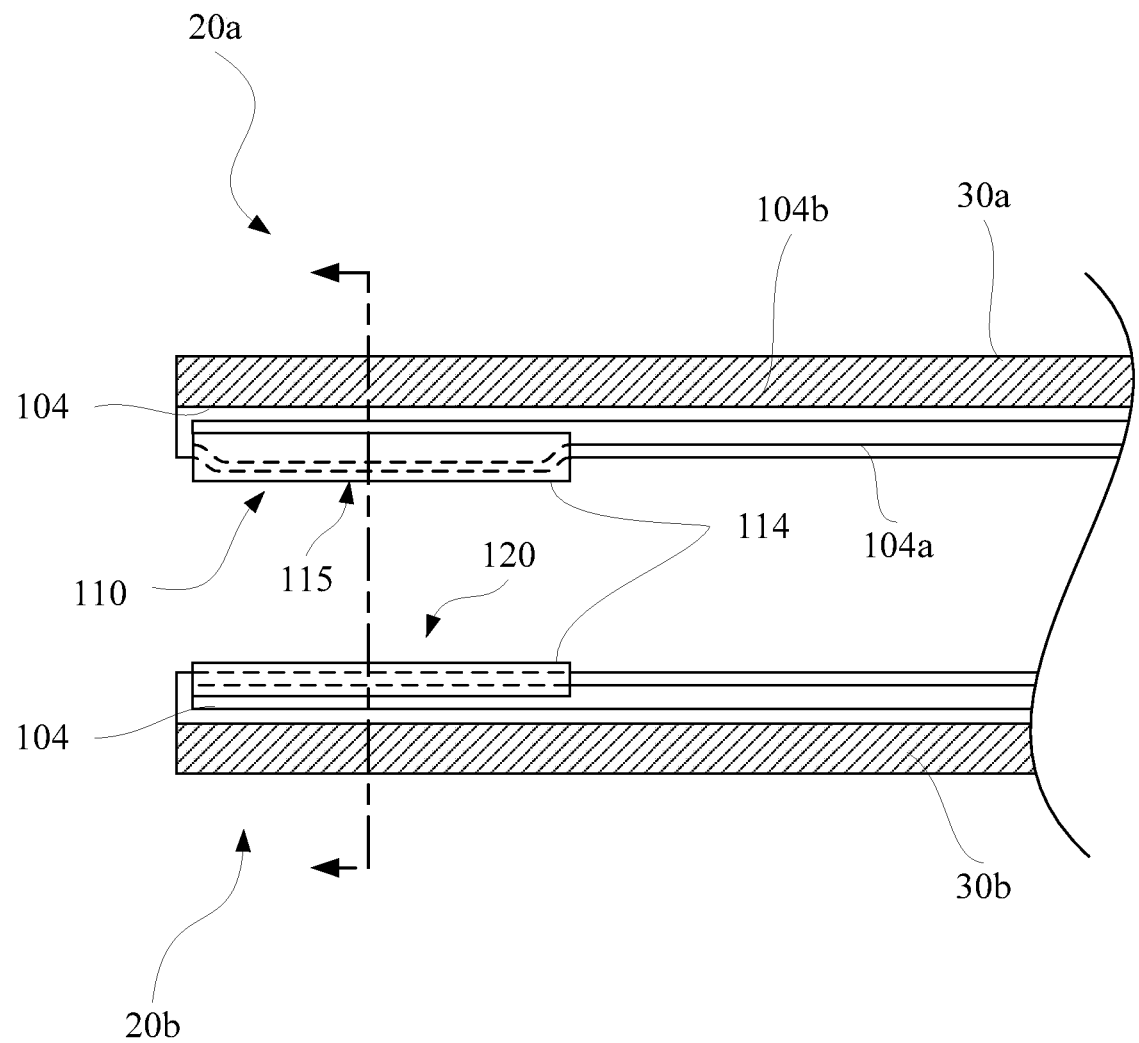
FIG. 8C shows a fragmented, side cross-sectional view of an another alternate configuration for the tip of a surgical sealing instrument according to principles of the present invention.
Figure 8D:
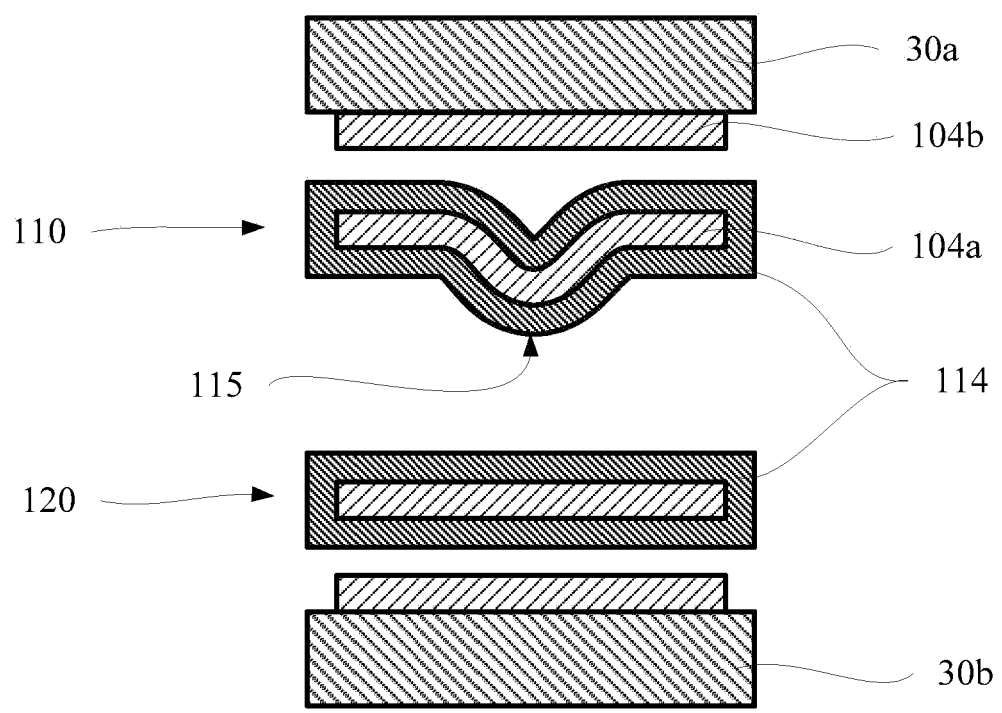
FIG. 8D shows an end cross-sectional view of the tip of the surgical sealing instrument of FIG. 8C.

Turning now to FIG. 8C, there is shown a fragmented, side cross-sectional view of another configuration for tips of a surgical sealing and/or cutting instrument according to principles of the present invention. For clarity purposes, the cross-hatching of the active elements 110, 120 has been removed. FIG. 8D shows an end, cross-sectional view of the thermally active elements of FIG. 8C. The tips 20A, 20B may include active element(s) 110, 120. Each active element 110, 120 may comprise a conductor 104 having a ferromagnetic coating 114 disposed thereon, similar to the active element shown in FIGS. 8A and 8B. However, it will be appreciated that only one active element need generate thermal energy which is conducted to a duct or tissue according to principles of the present invention as explained in more detail below. As best shown in FIG. 8D, the active element 110 may be formed such that there is a cutting zone 115, formed by a protrusion, rib, etc., and a sealing zone 103 in the ferromagnetic heating region. As shown in FIG. 8D the cutting zone 115 is a protrusion which extends away from the generally planar surface which forms the sealing zone 103 of the active element. When a surgeon squeezes the arms 30A, 30B of the instrument together to cause the active elements 110, 120 to contact the duct or tissue, an increased amount of pressure will be applied to the duct or tissue at the location of the protrusion of the cutting zone 115. Heat generated by active elements 110, 120 is conducted to the duct or tissue, with a higher thermal density at the location of the cutting zone 115. Thus, a better seal may be achieved at the location of the cutting zone 115, or the duct or tissue may be severed along the cutting zone 115 due to the increased amount of pressure while areas of the duct or tissue in the sealing zone 103 may be sealed.

As explained above, a higher thermal density is required to cut a duct or tissue as compared to sealing the duct or tissue. To increase the thermal density along the cutting zone 115 the pressure applied and/or the heat conducted to the duct or tissue at the location of the cutting zone must be increased. Thus, as shown in FIG. 8D, the protrusion may provide increased pressure applied to the duct or tissue at the location of the cutting zone 115, thereby allowing the duct or tissue to be cut along the cutting zone 115 while being sealed along sealing zones 103. Thus, a single application can be used to both cut and seal.

Active elements may be constructed to have a variety of shapes in order to create a cutting zone and sealing zone similar to the cutting zone 115 and 103 discussed in connection with FIG. 8C. For example, FIGS. 8E through 8P show various active elements having different shapes or elements which may be used to create a cutting zone and sealing zone. These active elements could be used in conjunction with forceps or other thermally active surgical instruments shown herein.

It will be appreciated that the scope of the invention is not to be limited by the embodiments shown in FIGS. 8E through 8P, rather, FIGS. 8E through 8P are being provided for illustrative purposes only. Furthermore, for clarity, FIGS. 8E through 8P only show the active elements 110, 120, but it will be understood that the other elements of a sealing and/or cutting instrument according to principles of the present invention disclosed herein (e.g. the sealing and/or cutting instrument of FIG. 8C) would be associated with the active elements 110, 120 shown in FIGS. 8E through 8P.

While FIG. 8E shows an active element 110 (similar to the active element 110 shown in FIG. 8B) having a ridge extending along the planar surface of the upper active element 110 to form the cutting zone 115 and sealing zones 103 adjacent to the cutting zone 115, the projection forming the cutting zone 115 could be on the lower active element 120. (It will be appreciated that elements 110 and 120 as shown in FIGS. 8A-8P can function both as a cutting element and a sealing element or portions thereof.

According to one aspect of the invention the structure shown as element 120 may not be a ferromagnetic coated conductor. In fact, the structure 120 may only be a support structure (e.g. not a thermal element) which provides a compressive surface opposite active element 110. Alternatively, the active element 120 may generate heat to seal and/or cut a duct or tissue and have a ridge forming a cutting zone 115, while the active element 110 is a support structure for use as a compressive surface opposite active element 120 as shown in FIG. 8F.

FIG. 8G shows and active element 110 similar to that shown in FIG. 8E. The active element 120, however, differs from the active element 120 shown in FIG. 8E in that the active element 120 of FIG. 8G comprises a recess 117, or quasi-complimentary receptacle, to alter the compression force applied to a duct or tissue when the active elements 110 and 120 are squeezed together to engage the duct or tissue.

FIG. 8H shows and active element 120 with a sharp cutting zone 115 to facilitate cutting of a duct or tissue. The compressive force applied to a duct or tissue along the cutting zone 115 may be altered by including a recess 117 on active element 110 positioned generally opposite the cutting zone 115. While not shown in the drawings for brevity, the active element 110 of FIG. 8G could be combined with the active element 120 of FIG. 8H to form protrusions in alignment or out of alignment with one another to provide a desired cutting dynamic.

Figure 8I:
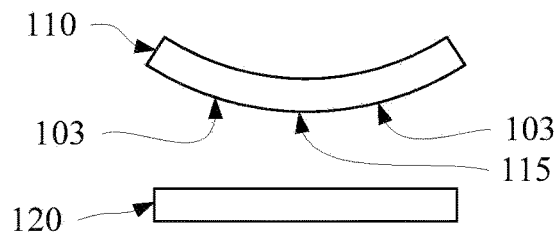
Figure 8J:
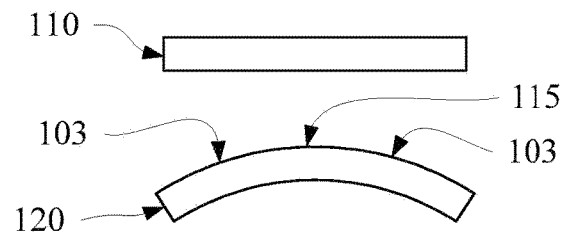

FIGS. 8I and 8J show an arcuate active element 110 and an arcuate active element 120, respectively. A cutting zone 115 may be formed about the apex of the curved or arcuate active elements 110 (FIG. 8I) and 120 (FIG. 8J) due to the increased amount of compressive force that will be applied to a duct or tissue at this location as compared to the compressive force that will be applied to the duct or tissue adjacent the cutting zone 115 at sealing zones 103.

Figure 8K:
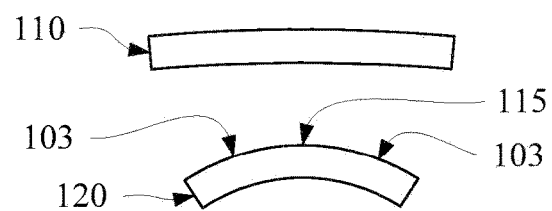
Figure 8L:
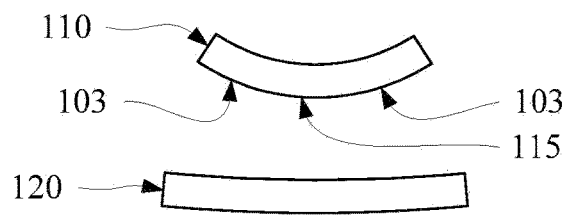

The compressive force applied along the cutting zone 115 shown in FIGS. 8I and 8J may be altered by matching the curved or arcuate active elements with an opposing active element that is also curved, as shown in FIGS. 8K and 8L. For example, the arcuate active element 120 shown in FIG. 8K may be paired with an arcuate active element 110. The degree of curvature of the arcuate active element 110 may be less than the degree of curvature of active element 120, and the degree of curvature of either (or both) the active element 120 and 110 can be adjusted to alter the compressive force applied to a duct or tissue. As shown in FIG. 8K, the arcuate active element 120 may curve in the same direction as arcuate active element 110 in a quasi-complimentary orientation. Alternatively, the compressive force along cutting zone 115 may be substantially increased relative to the compressive force applied along sealing zone 103 by having arcuate active elements curved in opposite directions from each other, such as is shown in FIG. 8P.

Figure 8M:
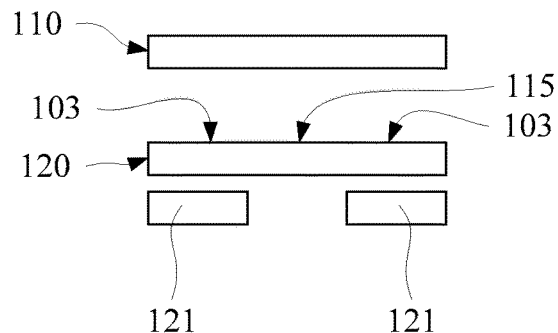
Figure 8N:
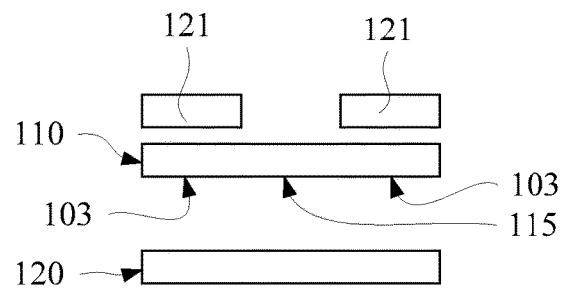

Cutting zones 115 and sealing zones 103 may also be created by altering the thermal conductivity along the surface of one of the active elements, as shown in FIGS. 8M and 8N. For example, active element 120 in FIG. 8M may be a support structure for providing a compressive surface opposite active element 110. One or more heat sinks 121 may be disposed adjacent the active element 110 (FIG. 8M) or 120 (FIG. 8N) to form a sealing zone 103 along a portion of the active element 110 to draw away a greater amount of heat from the active element on a portion thereof. As shown in FIGS. 8M and 8N, a the spaced apart heat sinks 121 disposed adjacent to the active element 120 and 110, respectively, may be used to create a cutting zone 115 located generally in the center of the active elements with sealing zones 103 on both sides of the cutting zone 115, as the heat in the center portion is not drawn away by the heat sinks.

Figure 8O:
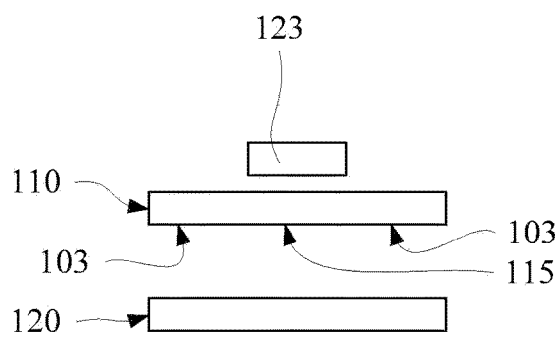
Figure 8P:
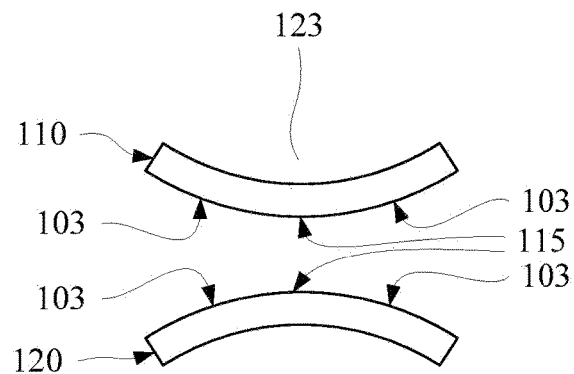

FIG. 8O also shows an active element 110 having a cutting zone and sealing zones 103. Rather than drawing heat away from sealing zones 103 as discussed above relative to FIGS. 8M and 8N, a heat spreader 123 of moderate thermal conductivity may be used to concentrate a greater amount of heat along a cutting zone 115 as compared to a sealing zone 103. As shown in FIG. 8O, the heat spreader 123 may be disposed adjacent the active element 110 in a central location so as to create a cutting zone 115 located generally in the center of the active element 110 with a sealing zones 103 on both sides of the cutting zone 115

Figure 9:
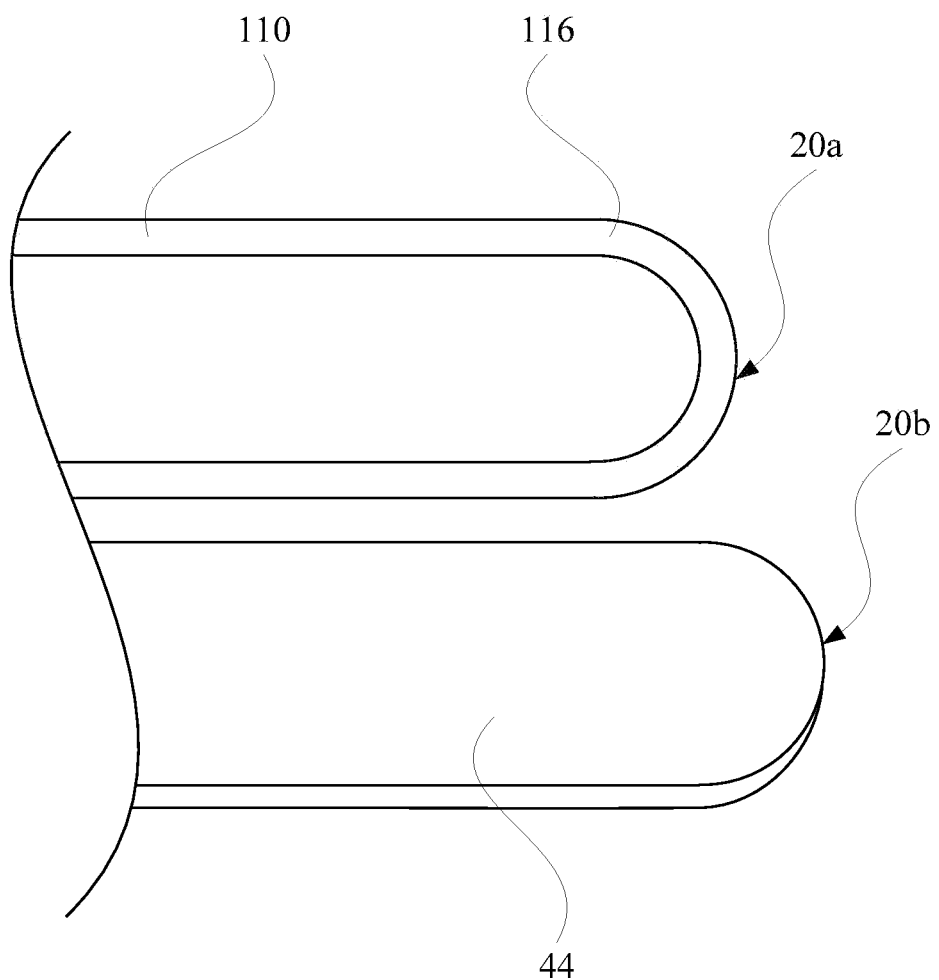
FIG. 9 shows a close-up, fragmented view of yet another alternate configuration of the tips of a surgical sealing instrument.

Turning now to FIG. 9, there is shown a fragmented, perspective view of the tips 20A, 20B of a sealing and cutting instrument, such as sealing forceps, according to one aspect of the invention. In contrast to FIG. 1, tip 20A in FIG. 9 may have an active element 110 comprised of only a rigid loop 116 forming a sealing and/or cutting element. The rigid loop 116 may be opposed to surface 44 of tip 20B and aligned in a generally horizontal orientation which would provide sealing and/or cutting at two points when disposed perpendicular to a duct. It will be appreciated, however, that the rigid loop 116 may be aligned in different orientations to achieve a more specific therapeutic effect, such as aligned vertically to achieve a single, more rapid cut.

Rigid loop 116 may be formed of a conductor wire having a ferromagnetic material disposed along at least a portion thereof, typically circumferentially about a portion of the conductor wire. The conductor wire may be of a sufficiently large gauge so that the rigid loop 116 substantially resists deformation when tips 20A and 20B are used to apply pressure about a tissue or duct. For example, to seal an artery it is important that sufficient pressure be applied to the artery so that the endothelium of opposing walls of the artery are adjacent each other. Then power may be supplied to the active element 110 to seal the artery. It will be appreciated that conductor wire is used herein for convenience only and those skilled in the art will appreciate that other conductive material may be used to form the rigid loop 116.

Sealing and cutting of a tissue or duct using tips 20A and 20B may occur sequentially. For example, the tips 20A, 20B may be placed around tissue to be sealed and the tips forced together so as to provide pressure on the tissue. Power may then be supplied to active element 110 to heat the tissue or duct. Initially, sealing of the tissue or duct will occur as the active element and/or the tissue or duct may not exceed approximately 100° C. as water evaporates from the tissue or duct, i.e. the temperature of the active element and/or the tissue or duct may be limited by the phase change of water in the tissue or duct as it evaporates. Once all water has evaporated, the temperature may then quickly rise to cut the tissue or duct.

It will be appreciated that sealing and cutting of a tissue or duct may be accomplished by supplying a constant power to the active element 110. For example, a low wattage may be supplied to the active element 110 to coapt lung tissue. The temperature of the active element may be about 100° C. until all water in the lung tissue evaporates. This may take approximately 40 seconds when the active element 110 is supplied with about 30 watts of electrical energy. Once the lung tissue becomes desiccated the temperature of the active element 110 may suddenly rise to commence cutting of the tissue.

Figure 10A:
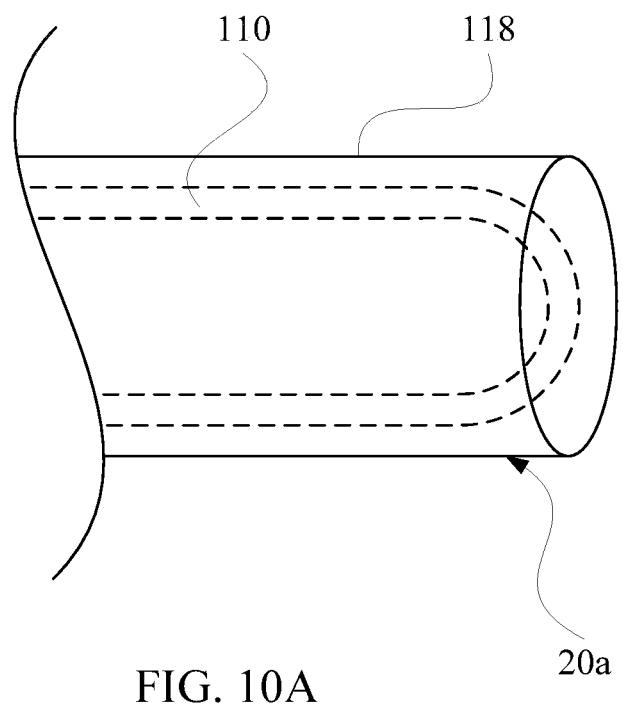
FIG. 10A shows a close-up, fragmented view of a tip of a surgical sealing instrument having a heat dispersing element.
Figure 10B:
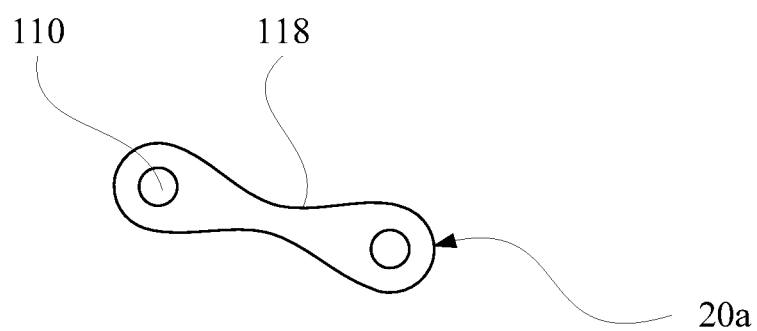
FIG. 10B shows an end view of the tip of FIG. 10A.

Turning now FIGS. 10A and 10B, there is shown an alternate configuration of a tip 20A in perspective and from a cross-sectional view, respectively. Tip 20A may have an active element 110 disposed in a heat dispersing member 118. The heat dispersing member 118 conducts heat away from the active element 110 so that heat may be applied to a tissue or duct more uniformly along an outer surface of the heat dispersing element 118. Use of a tip 20A having a heat dispersing member 118 may be more desirable when a therapeutic procedure does not require cutting of the tissue or duct. Because heat is less concentrated at a discrete location along the tissue or duct, it may be treated using tip 20A without being cut.

The heat dispersing member 118 may be a material that resists sticking to a tissue when thermal energy is applied to the tissue by active element 110, such as Teflon®, Kapton®, etc. It will be appreciated that tissue may stick to the active element 110 until it reaches a sufficiently high temperature, e.g. 300° C. However, active element 110 may not be used at such high temperatures during some therapeutic procedures, such as vascular shrinkage in aneurism preparation for clipping. Thus, use of a non-stick heat dispersing member 118 during such procedures may be necessary to avoid tissue sticking to the active element 110.

It will be appreciated that use of a non-stick material such as Teflon®, Kapton®, etc., may be used on various surfaces or elements in the embodiments described herein. For example, it may be desirable to include a non-stick material on surface 44 opposed to active element 110 in FIG. 9 to ensure that heated tissue does not stick to surface 44. A non-stick material may be desirable in therapeutic procedures involving welding, sealing, coapting, and/or homeostasis which involve temperatures at or below approximately 100° C.

Figure 11:
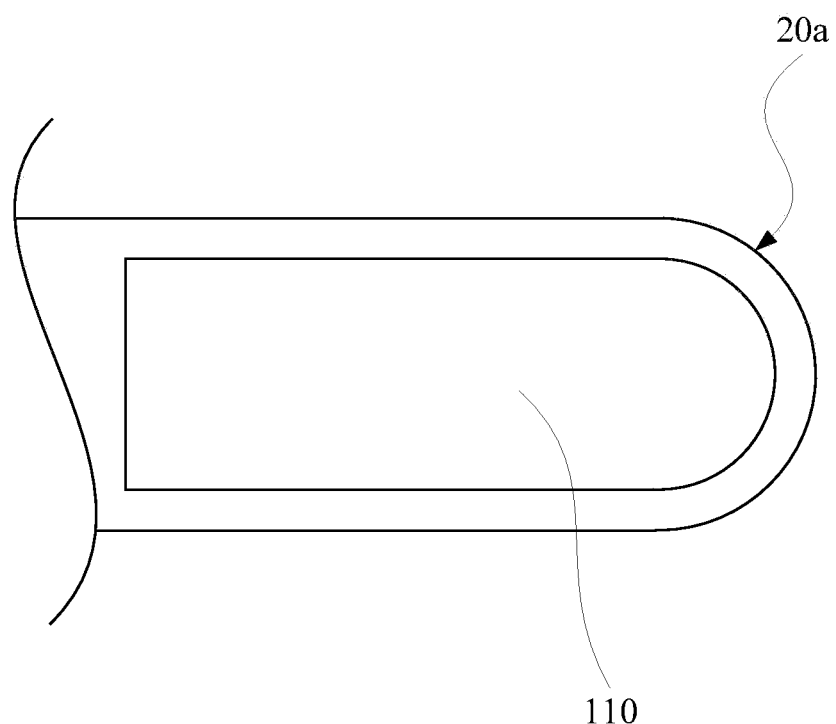
FIG. 11 shows a close-up, fragmented view of an alternate tip of a surgical sealing instrument.

Turning now to FIG. 11, there is shown another configuration of tip 20A. Tip 20A may include active element comprised of a ferromagnetic material in sheet form, such as Alloy 152. The sheet of ferromagnetic material may be placed over a surface mounted inductive coil (not shown) to form an active element 110 and achieve a broad active surface that may be used to treat tissue. Further, direct electrical connection may be provided to the sheet of ferromagnetic material, instead of inductive coupling. This may produce sufficient heat to deliver the desired therapeutic effect. It will be appreciated that it may be desirable to use a thin sheet of ferromagnetic material as the time to heat and cool the tip 20A is dependent on the thermal mass of the material.

Figure 12:
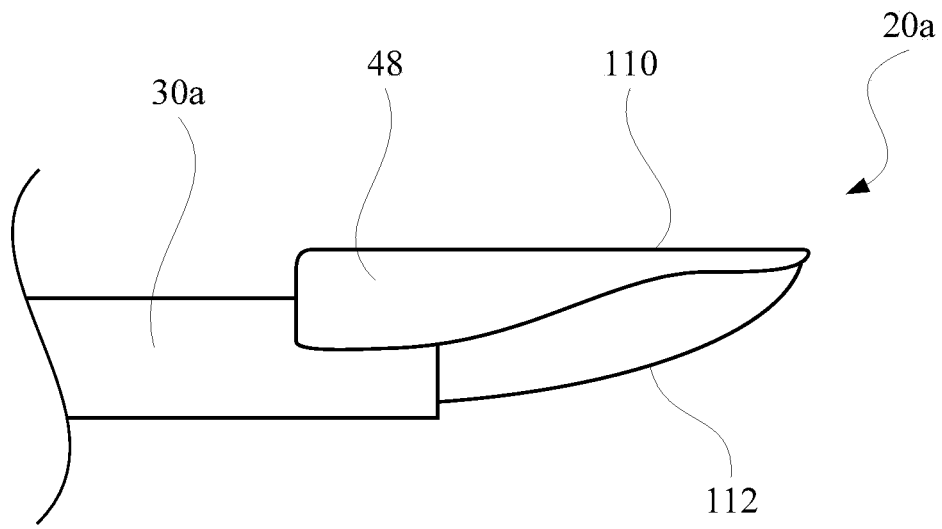
FIG. 12 shows a fragmented, side view of another tip of a surgical sealing instrument according to principles of the present invention.
Figure 13:
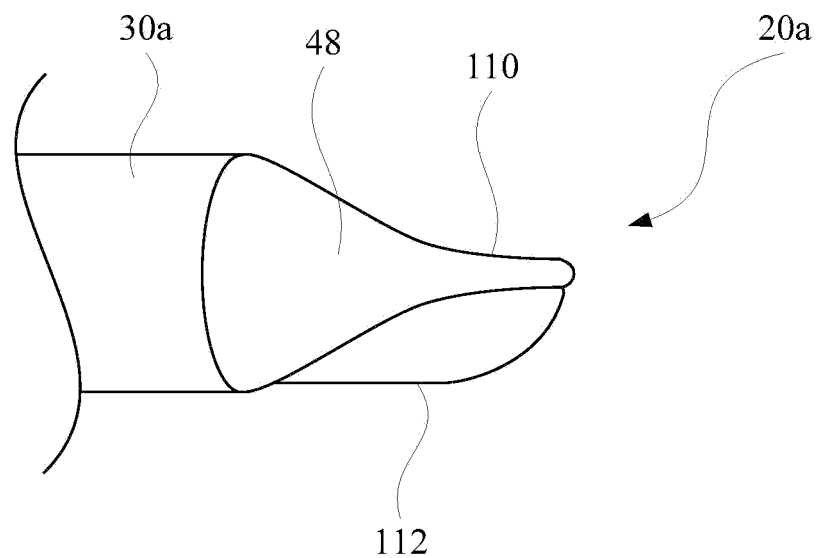
FIG. 13 shows a fragmented, top view of the tip of FIG. 12.

Referring now to FIGS. 12 and 13, there is shown still another configuration of tip 20A. Tip 20A may be attached to an arm 30A and include an active element 110 having a sealing member 48 and a cutting member 112. Sealing member 110 may have a relatively broad surface which may be used to seal, weld, or coapt tissue or a duct or to achieve homeostasis. Sealing member 110 may, for example, be a sheet of ferromagnetic material disposed on a conductor similar to that described in FIG. 11, or a ferromagnetic coating plated on a flattened conductor as described, for example, in FIGS. 8A-8C.

The cutting member 112 may be a thin wire, such as a wire coated with a ferromagnetic material which may allow a surgeon to cut a tissue or duct at a more precise location. A surgeon may be able to cut a tissue or duct using cutting member 112 and then use the reverse side of the tip, the sealing member 48, to achieve homeostasis. Alternatively, a surgeon may use the sealing member 48 to seal a tissue or duct and then flip the tip 20A over to make a precise cut using the cutting member 112.

Figure 14:
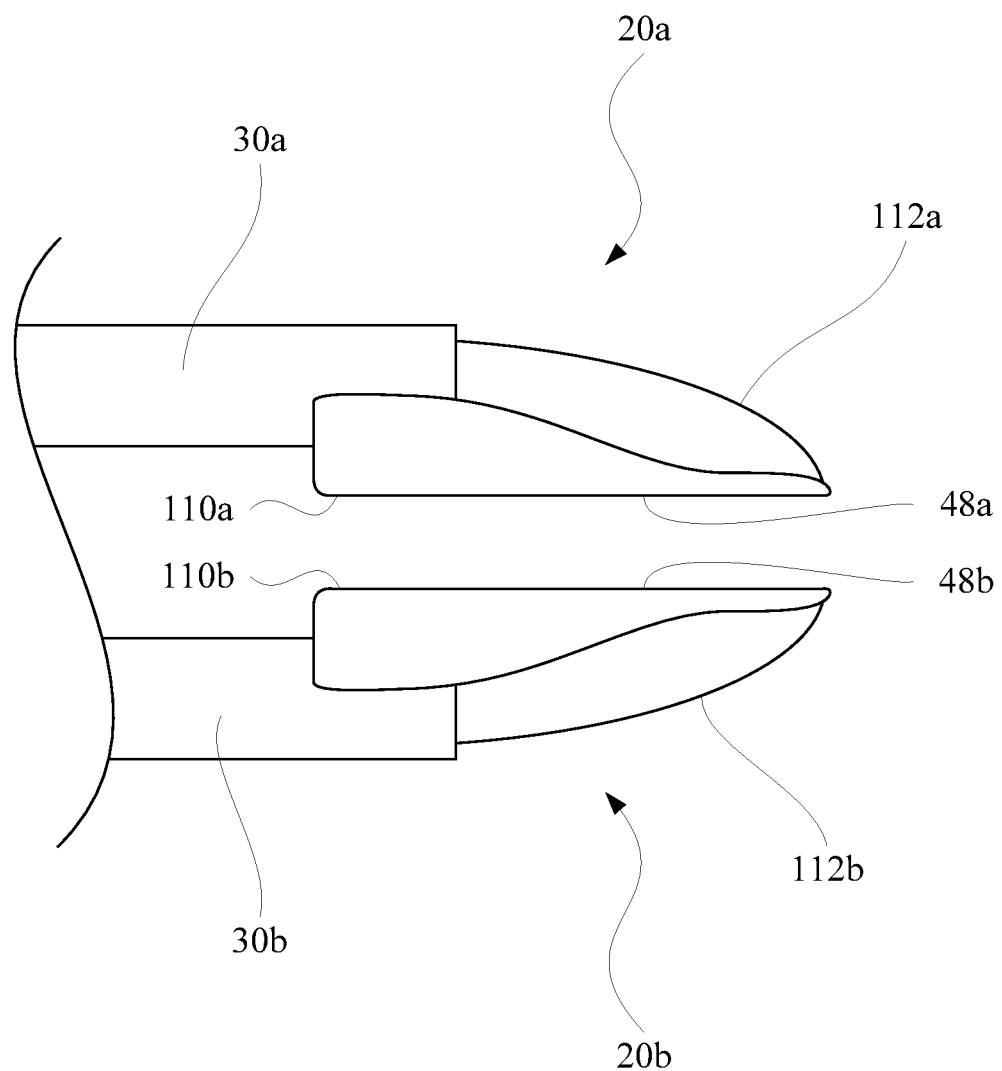
FIG. 14 shows a fragmented, side view of the tips of a surgical sealing instrument.

A surgical instrument may include more than one of the tips shown in FIGS. 12 and 13 which are disposed opposite each other as is more clearly shown in FIG. 14. Tissue or a duct may be grasped between sealing members 48A and 48B. Sealing members 48A and 48B may then be used to apply pressure to the tissue or duct. Power may then be supplied to the sealing members to seal the tissue or duct.

Once the tissue is sealed, a surgeon may use either of the cutting members 112A, 112B to cut and/or remove tissue if needed or desired, or the sealed tissue may be left as is if there is no need to remove tissue.

While some of FIGS. 1-13 show a single active surfaces or elements on one side of the instrument, it will be appreciated that an instrument may have complementary active surfaces 40 or elements 110 which either align with or are slightly offset from the other active surface to ensure sealing and cutting of thicker ducts and tissues, such as that which is in FIG. 14. This may be in the context of forceps, scissor-like instruments or a host of other surgical devices.

Figure 15:
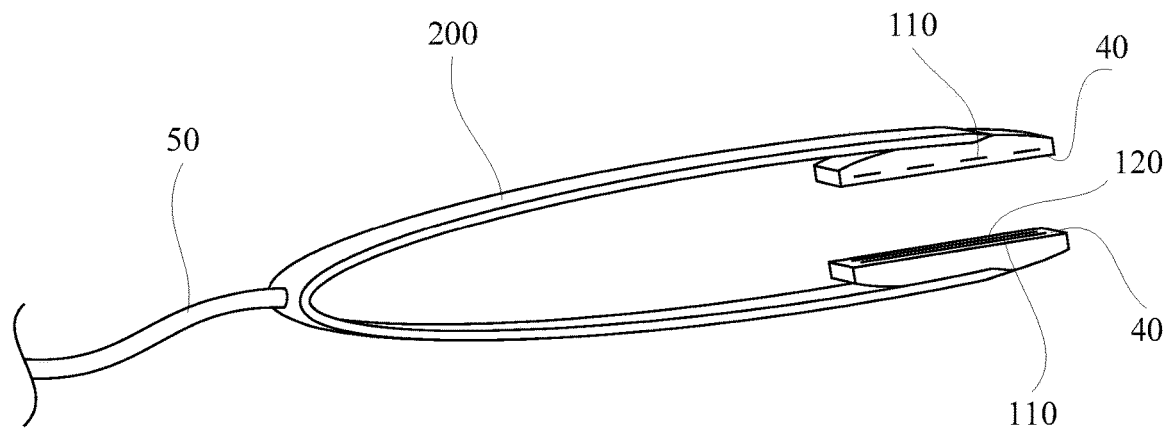
FIG. 15 shows a perspective view of a surgical instrument having cooperating elements.

FIG. 15 shows a perspective view of a surgical instrument 200 having cooperating opposed active surfaces 40 with sealing and cutting elements 110, 120 disposed on or extending from the active surfaces in order to seal and cut a duct, tissue, etc., from opposing sides. The surgical instrument 200 may be powered by a cable 50 in a manner similar to that discussed with respect to FIG. 1.

The surgical instrument 200 can be used similar to forceps to seal and cut veins and ducts, or can be used in a manner more analogous to scissors. For example, in FIG. 1, active element(s) of the surgical instrument 200 are being selectively activated to seal and cut tissue, such as lung tissue, or other tissue in the body. In such a manner diseased or damaged tissue can be cut out of the body while also sealing the remaining tissue against the loss of blood or other fluid and against the entry of bacteria, etc. The surgical instrument 200 can be placed on an initial portion of tissue and the sealing active element(s) (e.g. 120) activated to seal the tissue and then the cutting active element(s) (e.g. 110 or the sealing active element at different power) activated to cut through the tissue. The surgical instrument 200 may be advanced and the procedure repeated until the undesired tissue is completely cut away.

Figure 16:
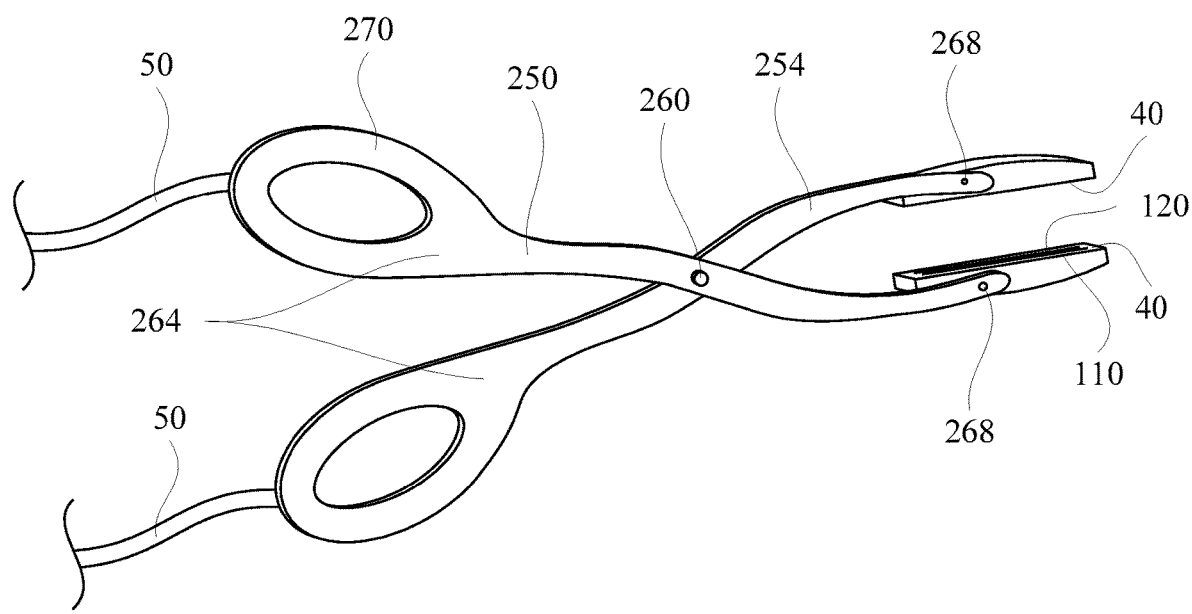
FIG. 16 shows a perspective view of another surgical instrument made in accordance with the present invention.

Turning now to FIG. 16, there is shown a perspective view of an alternate configuration of a surgical instrument 250 for use in the present invention. Rather than operating like a pair of forceps as shown in FIG. 15, the surgical instrument 250 functions in a manner more analogous to scissors. Each active surface 40 is attached to an arm 254 which extends to a pivot point 260 and then to a handle portion 264 formed by finger holes 270 or some other gripping structure.

The active surfaces 40 and/or active elements 110, 120 may be formed as part of the arms 254, or may be attached to the arms, such as by pivots 268, to allow the active surfaces or elements to adjust relative to one another and apply pressure more uniformly on a tissue than would occur in a scissors where there may be greater pressure adjacent the pivot point 260. Thus, the sealing may be more consistent as the active surfaces 40 and elements 110, 120 remain more parallel.

In use, the surgeon would position the active surfaces 40 along the area to be cut and apply force on the handle portion 264 while power is delivered through the cable(s) 50 from a power supply to the active elements to thereby seal and cut tissue. If necessary, the active surfaces 40 could then be advanced along the tissue and the process repeated.

FIG. 17 shows a perspective view of a surgical instrument 200 having a rigid loop 116 cooperatively opposed to a surface 44. The surgical instrument 200 may be powered by a cable 50 connected to a power supply in a manner similar to that discussed with respect to FIG. 1. One advantage of surgical instrument 200 having a rigid loop 116 is that a user of the surgical instrument 200 may be able to better view the tissue or duct that is to be sealed and/or cut.

A sensor 119 may be disposed in communication with the surgical instrument 200. As shown, the sensor 119 may be disposed on the surface 44 and used to monitor electrical properties of the tissue or duct. For example, when the surgical instrument 200 is being used to seal and cut a tissue, evaporation of water may cause the capacitance of the tissue to change and shift the standing wave ratio ("SWR") of the applied electrical energy. The sensor may detect the shift in the SWR and provide a signal of the transition from sealing to cutting of the tissue by the surgical instrument. Thus, the sensor 119 may provide the surgeon with an indication of the effectiveness of the seal and the status of the sealing/cutting taking place.

The sensor 119 may also monitor temperature of the interface between the active element 110 and the tissue. Once a sufficient temperature is achieved to cut the tissue, a signal may be generated to notify the surgeon that the tissue has been cut or is being cut. Thus, for example, the element 110 may hold at 100° C. for a period of time. If pressure is being applied to duct, etc., this will correspond with sealing. Once sealing it complete, the water in the tissue will be consumed and the temperature of the element 110 will suddenly rise, indicating transition in to the cutting phase. To provide control, the instrument 200, or some related structure, may advise the physician which phase is currently being undertaken, or it may advise the physician that sealing is complete and that cutting can commence.

The surgical instrument 200 may include additional, or alternate, sensors to monitor sealing and cutting of a tissue or duct. For example, a thermocouple may be disposed integrally with the surgical instrument to monitor temperature as the procedure progresses from sealing to cutting and/or when cutting of the tissue is complete. Alternatively, the electrical properties of the conductor of active element 110 may indicate when sealing and/or cutting of the tissue is complete. For example, if active element 110 is comprised of a tungsten conductor coated with a ferromagnetic material, then the resistivity of the tungsten conductor may be monitored to determine when sealing and/or cutting is complete. As water evaporates from the tissue, the resistivity of the tungsten conductor may increase. Thus, the resistivity of the tungsten conductor may be correlated with the completion of tissue sealing.

Figure 18:
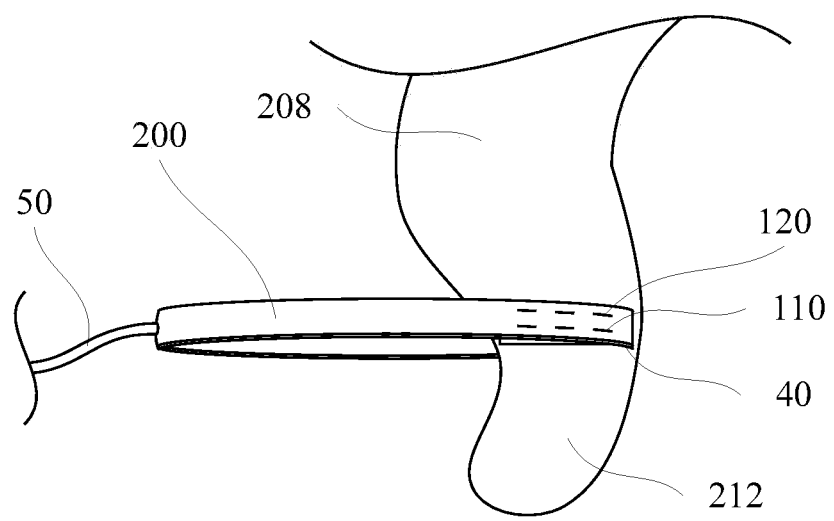
FIGS. 18 and 19 show surgical instruments being used on tissue in accordance with the present invention.

FIG. 18 shows a surgical sealing and/or cutting instrument 200 being used to treat tissue 208. The surgeon may position the tissue 208 between the active elements 110, 120. The active elements are then actuated to seal off a section of the tissue 212. If so desired the section of tissue 212 can be cut using the instrument 200 and removed from the surgical site, thereby leaving the main tissue 208 sealed along the incision.

Figure 19:
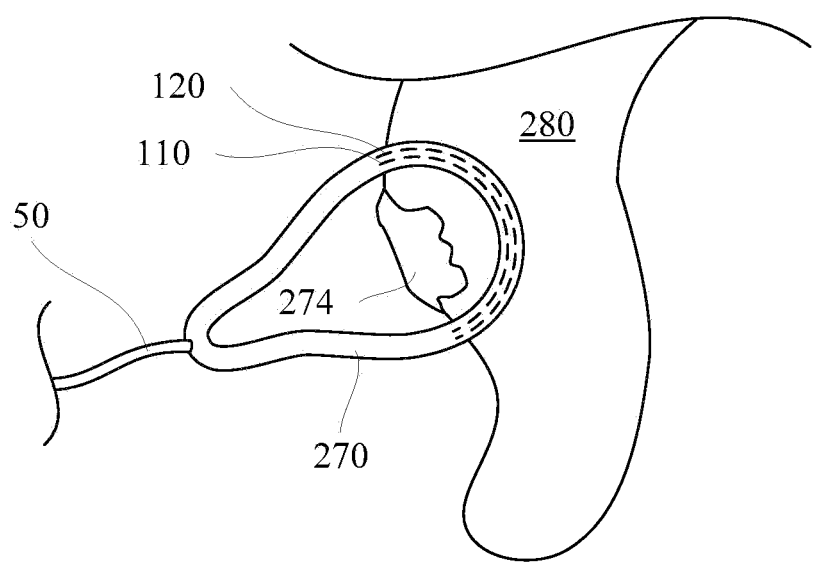

FIG. 19 shows an alternate configuration of a surgical instrument 270 being used to cut a tumor 274 from lung tissue. As was mentioned above, the active surface 40 and/or active elements 110/120 need not be linear and may be bendable. In FIG. 19, the elements are disposed in a generally semi-circular configuration so as to enable sealing around and cutting out of a tumor. (A complementary portion to that shown may engage the tissue on the opposing side and may lack any active elements so that it merely engages the tissue, or may have one to two elements for promoting sealing and cutting). In use the active elements 110, 120 are positioned on the lung tissue just beyond the area to be removed. The elements are then powered from a power supply via cable 50 to seal off the lung tissue 280 (along thermally active element 120) and to cut the portion of the lung tissue containing the tumor 274 (along thermally active element 110). Thus, the tumor is cut away as the remaining lung tissue is sealed to thereby prevent air and blood leakage, etc.

Turning now to FIGS. 20-28, various tools with parallel linkages are shown which can be used, in accordance with one aspect of the invention, in conjunction with tissue sealing/cutting elements to selectively seal and cut or cut and seal ducts in a human or animal. As tissue bundles or ducts to be sealed are larger, parallel surface movement of the one or more treatment surfaces may be desirable. If an angular movement instrument is used with a larger tissue bundle, more pressure may be placed on the proximate portion, i.e. the portion of the bundle or duct that is closest to the pivot. This leaves the distal portion, i.e. away from the pivot, with less pressure. With less pressure, it is possible that the distal portion may receive little to no energy or pressure from one or more of the treatment surfaces 40, or may not be held in sufficient contact with adjacent tissue to form a good seal. With parallel movement surfaces, the tissue bundle may receive more-equal pressure on the proximate and distal portions. Thus the heat may be approximately equally distributed along the tissue bundle surface. This is particularly important when sealing large ducts or tissues.

For small ducts or tissue bundles, such as small blood vessels, forceps or jaws on a pivot (similar to scissors) may adequately approximate parallel movement for the small movement required. With larger ducts or tissue bundles, however, it may be desirable to choose a parallel surface movement linkage as discussed herein.

Figure 20:
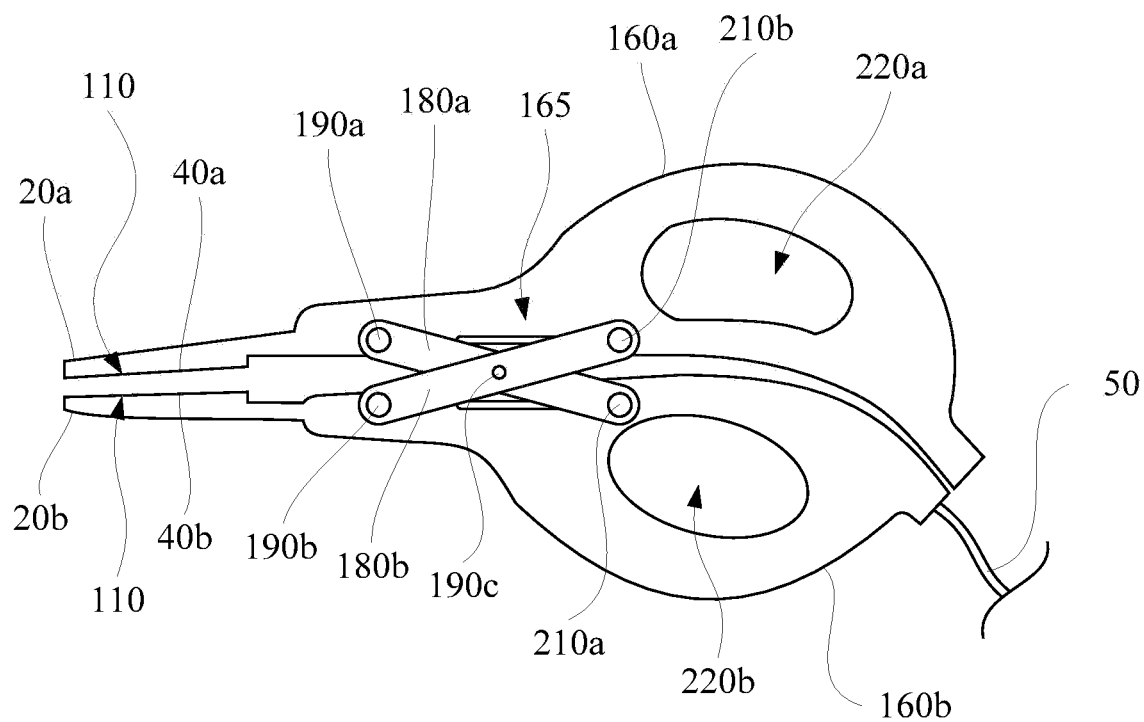
FIG. 20 shows a close-up, side view of the parallel movement surgical sealing and cutting tool in a nearly closed position.
Figure 21:
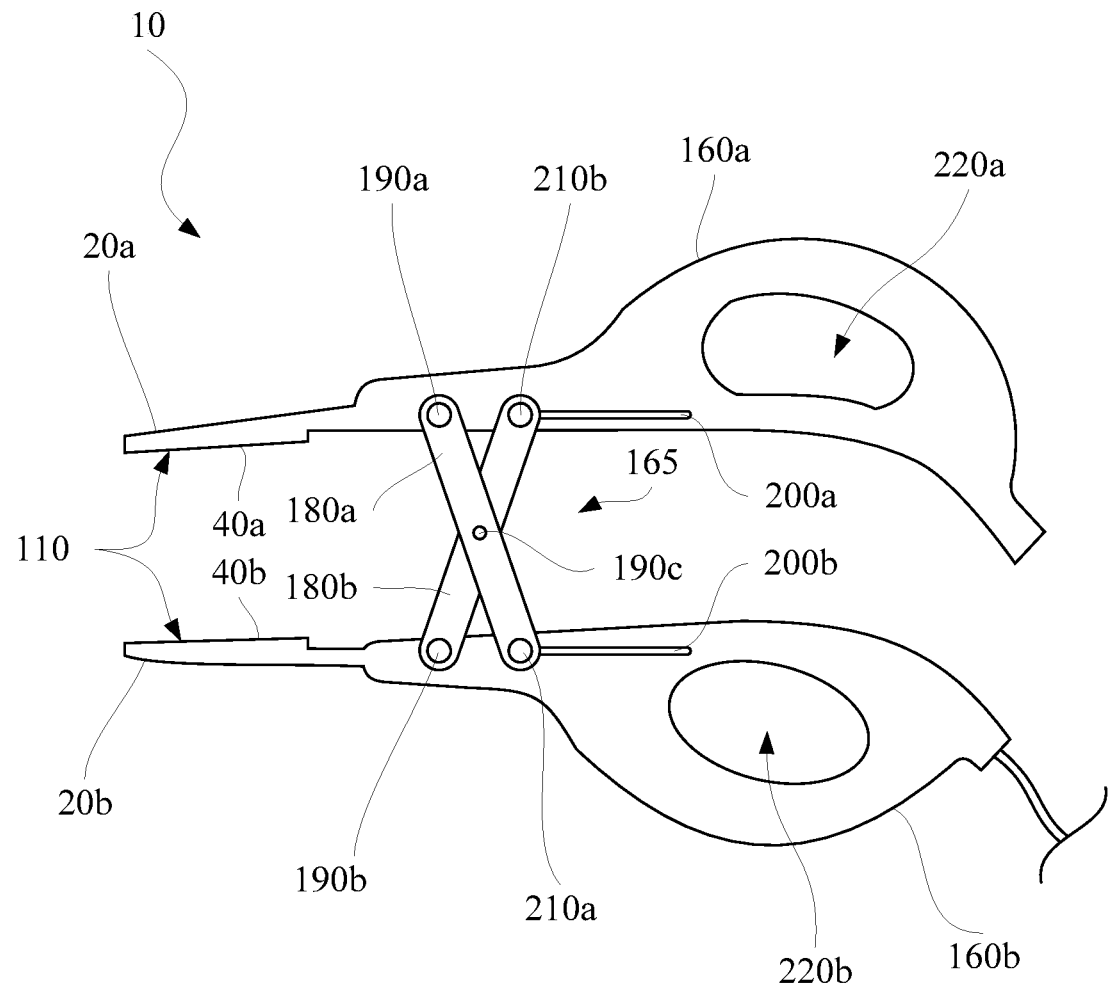
FIG. 21 shows a side view of the parallel movement surgical sealing and cutting tool of in an open position.

Turning now specifically to FIGS. 20 and 21, a side view of a parallel movement surgical sealing and/or cutting instrument, generally indicated at 10, is shown with the instrument in a nearly closed position (FIG. 20) and in an open position (FIG. 21). The instrument may include a parallel movement linkage, generally indicated at 165. Such a parallel linkage has been referred to as a pantograph linkage.

Two instrument halves 160A, 160B are connected by the parallel movement linkage 165 so as to enable a treatment or active surface 40A (or active elements 110 which may be embedded in or extend from the treatment surface and a treatment or active surface 40B—which may have similar active elements) to move in parallel with one another. The linkage has two arms or bars 180A, 180B that are fixed at one end via fasteners 190A, 190B to the two instrument halves 160A and 160B, respectively, and connected in the middle via a fastener 190C. The opposing end of the bars 180A, 180B may include fasteners 210A, 210B, respectively, or other connectors which move in linear tracks 200A, 200B (FIG. 6) in the two instrument halves 160A and 160B. When operated, the linkage causes a line defined by fastener 190A and second bar end fastener 210B to remain parallel to fastener 190B and second bar end fastener 210A while the distance between these lines are adjusted. This X linkage has been referred to as a pantograph linkage.

The instrument 10 may be operated with one hand. A user may insert their fingers into the openings 220A, 220B. Using the fingers, the user may separate the instrument halves 160A, 160B causing the instrument tips 20A, 20B to separate as well. Alternatively, the instrument halves 160A, 160B may be biased by a spring in the open position. A tissue bundle may be placed between the active surfaces 40A, 40B while the user may cause the instrument tips 20A, 20B to apply pressure to the tissue bundle by squeezing the instrument halves 160A, 160B together. One or both of the active surfaces 40A, 40B may contain one or more active elements 110 that may be activated at a first energy setting to seal the tissue bundle. The user may then activate the one or more active elements 110 (120, etc.) to cut the tissue bundle after sealing. The instrument may then be removed from the tissue bundle. The instrument 10 can move through tissue in a manner similar to scissors, but enables a physician to seal and cut the tissue, thereby avoiding the need to tie off blood vessel or sew up the tissue because the tissue was sealed as well as being cut.

Figure 22:
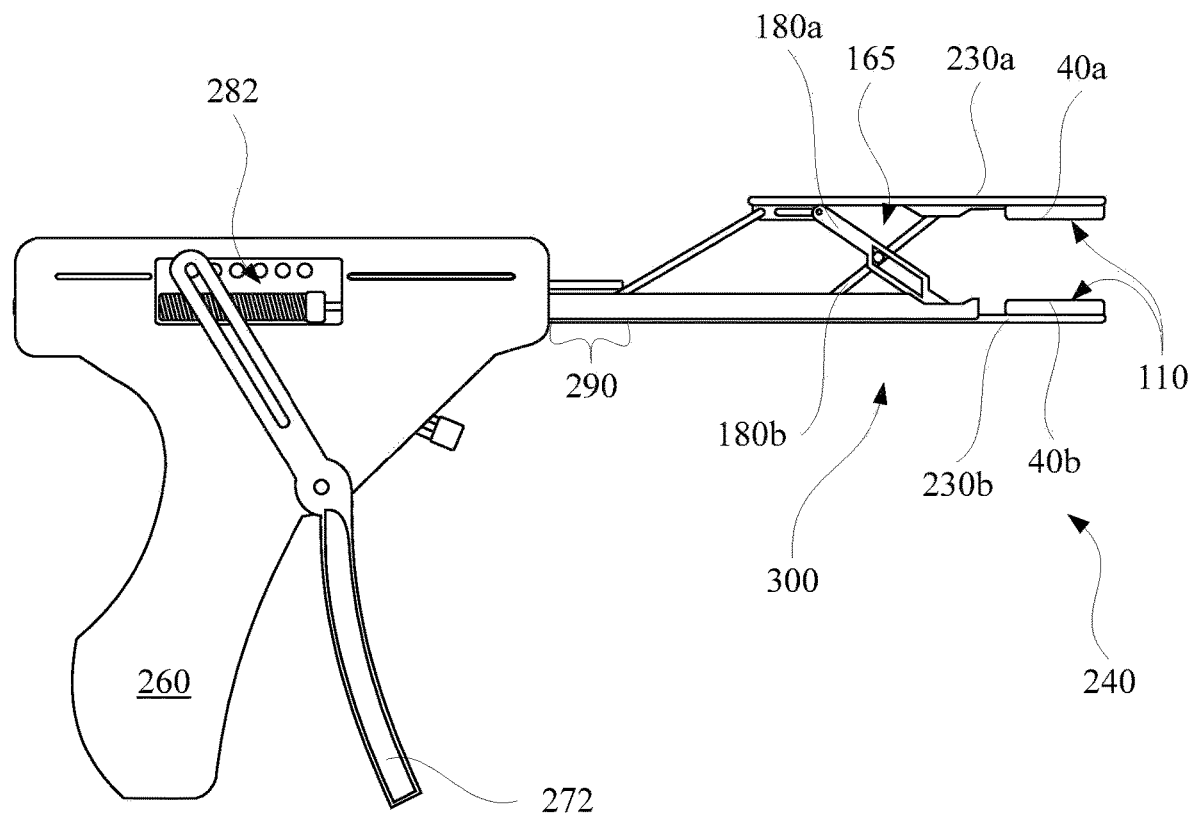
FIG. 22 shows a side, fragmented view of a parallel movement surgical sealing and cutting tool operable through a catheter or cannula with pistol grip, the sealing tool being in an open position.
Figure 23:
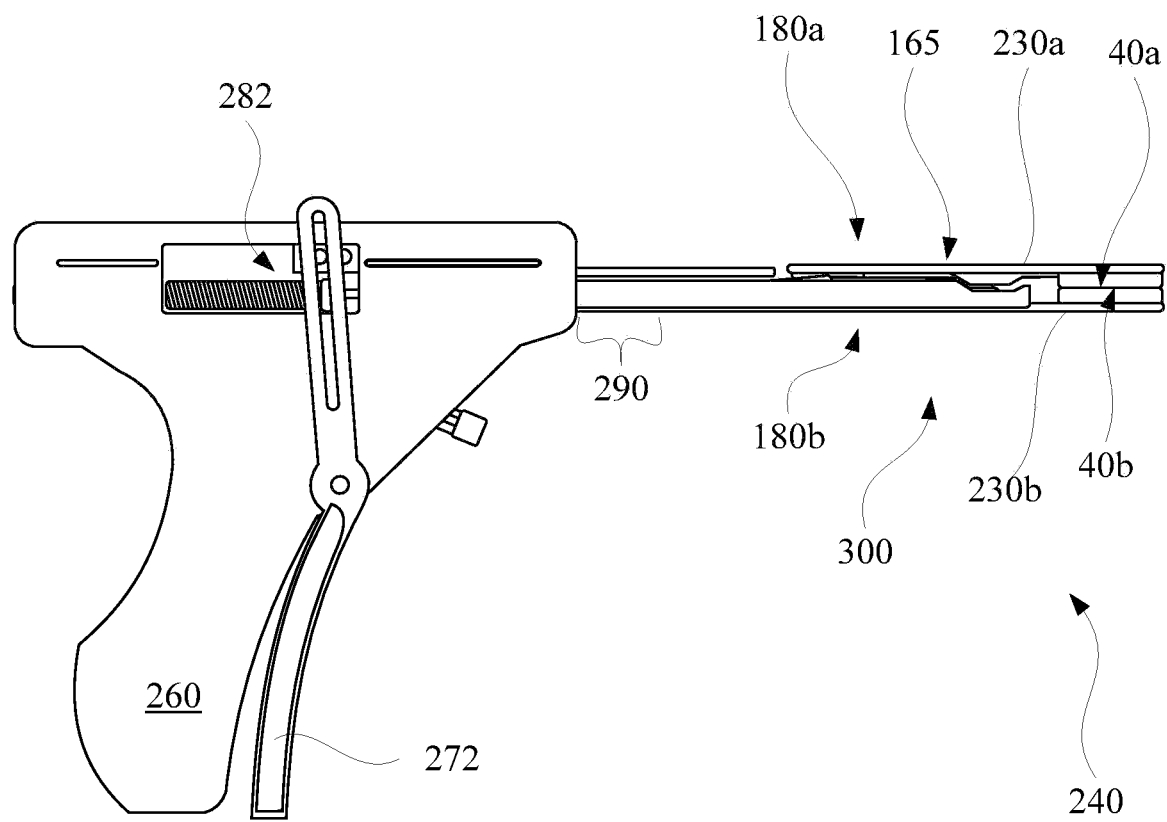
FIG. 23 shows the surgical sealing and cutting tool of FIG. 22 in a closed position.
Figure 24:
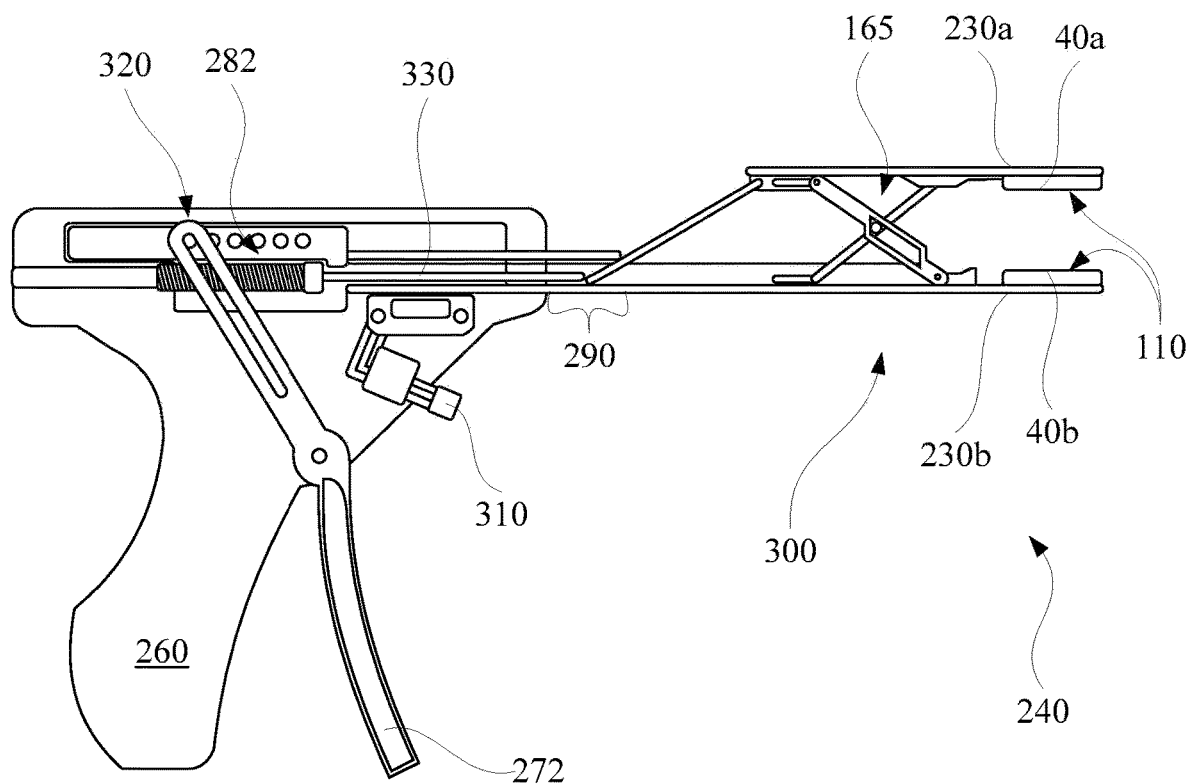
FIG. 24 shows a side, plan view of the surgical sealing and cutting tool of FIG. 22.

Turning now to FIGS. 22 through 24, side views of a parallel movement sealing and/or cutting instrument 240 operable through a small access port with a pistol grip are shown. The sealing and/or cutting instrument 240 may be biased into either the open or closed position depending on the use desired by the physician. In some cases, it may be desirable that a parallel movement sealing and/or cutting instrument fit within a trocar catheter or other cannula such as a laparoscope, in order to gain access to the body. This may be used, for example, when performing a laparoscopic tubal ligation or other laparoscopic procedure. Therefore, a parallel movement sealing instrument may include a configuration to fit within an access port when closed, while facilitating movement of the control mechanism outside the access port and actuation of the sealing elements at the opposing end of the sealing and/or cutting instrument. While the neck 290 shown in the figures may be short, it should be recognized that the neck may be extended for applications requiring longer access distance.

The parallel movement sealing instrument 240 (FIG. 22, normally open bias; FIG. 23, normally closed bias) may include a grip 260 trigger 272, bias mechanism 282, neck 290 and instrument end 300. The bias mechanism 282 may aid the instrument to reset to a known state, such as open or closed. The bias mechanism may be a spring or elastic member that resists stretching and/or compression. The neck 290 may be relatively short or long and may include a movement transfer linkage to take force applied by the trigger 270 and/or bias mechanism 282 and transfer the movement to the instrument end 300.

The instrument end 300 may include the parallel movement linkage 165 that enables a first treatment surface 40A to move in parallel with a second treatment surface 40B, such as the linkage described in FIGS. 20 and 21. One or both of the treatment surfaces 40A, 40B may include active elements 110, 120, etc. The treatment surfaces 40A, 40B may reside on tips 230A, 230B.

A user may apply the instrument by one or more of the following steps: selecting a surgical instrument having substantially parallel surface movement; causing the surfaces to be above and below a tissue to treat; reducing the distance between the surfaces so that the surfaces (or the elements if the elements extend from the surfaces) engage the tissue; and/or activating an active element on at least one of the surfaces to thereby seal and/or cut the tissue. In many applications, some force is applied to the tissue by the treatment surfaces or active elements while the tissue is being sealed and/or cut.

More specifically, a user may cause the instrument end 300 to become closed. The user may then insert the instrument 240 into an access port in the body. The instrument end 300 may then be opened and placed around a tissue bundle, duct, vessel, etc. The user may then apply the trigger 270 such that the tips 230A, 230B place pressure on the tissue being treated. One or both of the treatment surfaces 40A, 40B may contain an active element 110 that may be activated at a first energy setting to seal the tissue (via an electric current from a power source as discussed above). The user may then activate the one or more active elements 110 to cut the tissue bundle after sealing. The instrument 240 may then be removed from or advanced along the tissue bundle.

In FIG. 22, a normally open parallel movement sealing instrument 240 is shown. The normally open parallel movement sealing instrument may have the advantage of transferring the pressure applied to the trigger 272 to the tips 230A, 230B, such that the pressure on the tissue bundle may be regulated by the user's squeeze on the trigger 272.

In FIG. 23, a normally closed parallel movement sealing instrument 240 is shown. The normally closed parallel movement sealing instrument may have the advantage of consistent applied pressure by the bias mechanism 282 and the fact that a user would not be required to maintain pressure on the trigger 270 when closed on the tissue being treated.

Turning now to FIG. 24, a mechanical diagram of FIG. 22 is shown. An activation button 310 and trigger linkage 320 may be seen more clearly. The activation button may be used to apply power to the thermally active element 110. The trigger linkage 320 may include a post in a track allowing trigger 272 movements to be translated into linear movement of a rod 330. The rod 330 may be connected to the parallel movement linkage 165, allowing the transfer of force from the trigger 272 to parallel movement linkage 165.

Figure 25:
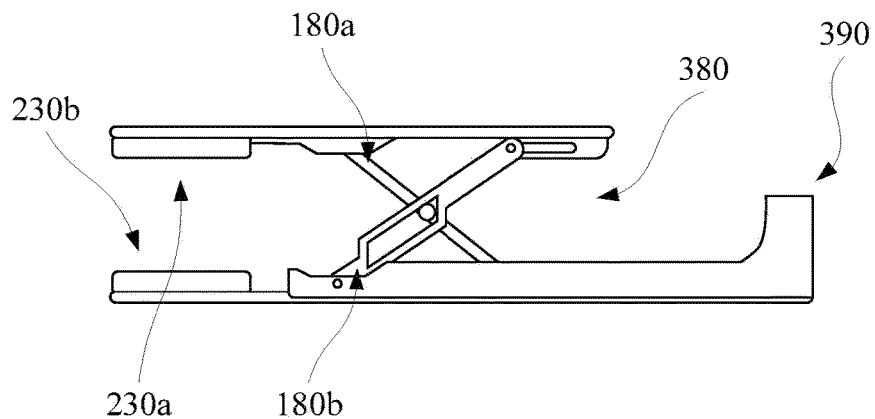
FIG. 25 shows a close-up, side view of a parallel movement end for a surgical sealing and cutting tool.

Turning now to FIG. 25, a parallel movement end 380 for the sealing instrument is shown. The parallel movement end 380 may be configured in a module 390. In one embodiment, the module 390 may be added to instruments that use forward and backward linear movement of a rod. For example, a sleeve could be attached to the module 390 and the rod attached to one of the bars 180a or 180b. As the rod moves forwardly and rearwardly, the tips 230A, 230B move toward and away from one another.

Figure 26:
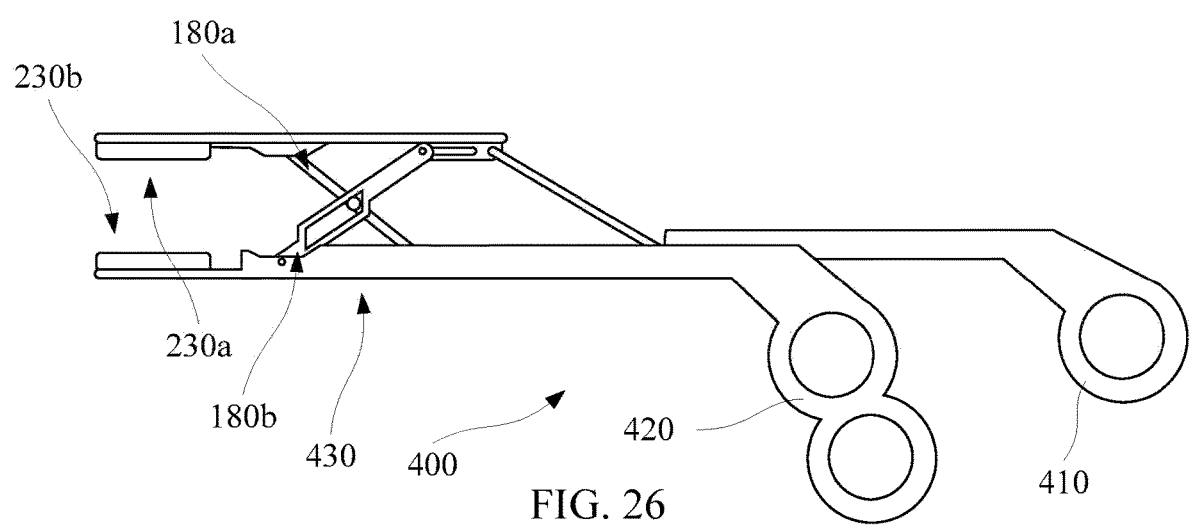
FIG. 26 shows a parallel movement surgical sealing and cutting tool with finger rings.
Figure 27:
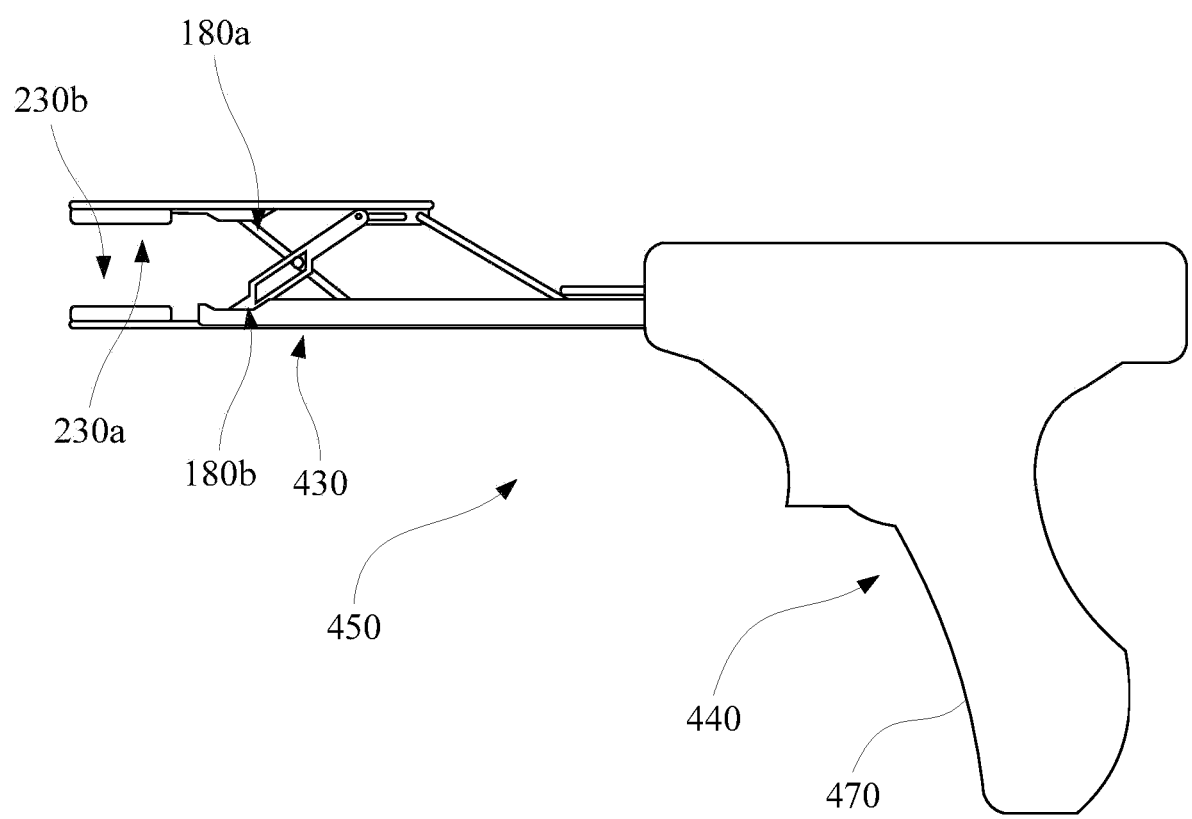
FIG. 27 shows a parallel movement surgical sealing and cutting tool with a squeeze grip.

Turning now to FIGS. 26 and 27, parallel movement sealing instruments 400, 450 are shown with alternate movement transfer linkages. FIG. 26 shows a movement transfer linkage with finger rings. Separation of a moving ring 410 from the stationary rings 420 may cause motion to be applied to the parallel linkage 430. Depending on how the moving ring and stationary ring are attached to the bars 180A, 180B forming the parallel linkage, moving the moving ring 410 toward the stationary ring 420 will either open or close the space between the tips 230A, 230B.

FIG. 27 shows a sealing instrument 450 with a movement transfer linkage 430 connected to a handle 440 with a squeeze grip trigger. Application of pressure to a front end 470 of the grip may cause the movement of the squeeze trigger to be transferred to the parallel linkage 430.

Figure 28:
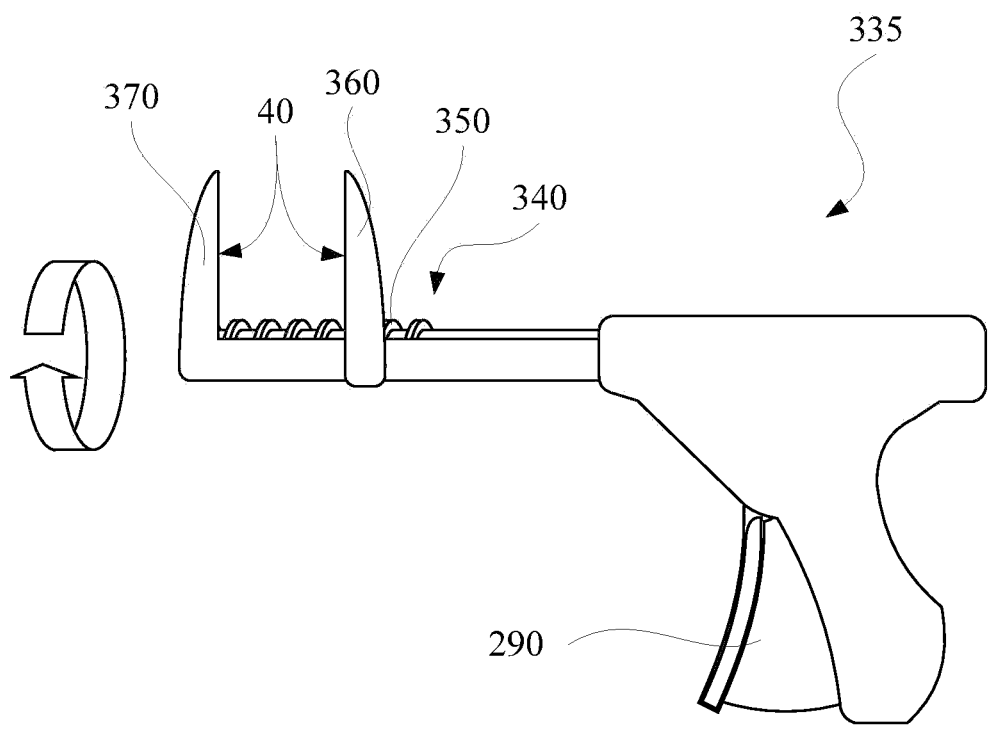
FIG. 28 shows a side view of an alternate embodiment of a surgical instrument made in accordance with principles of the present invention.
Figure 29:
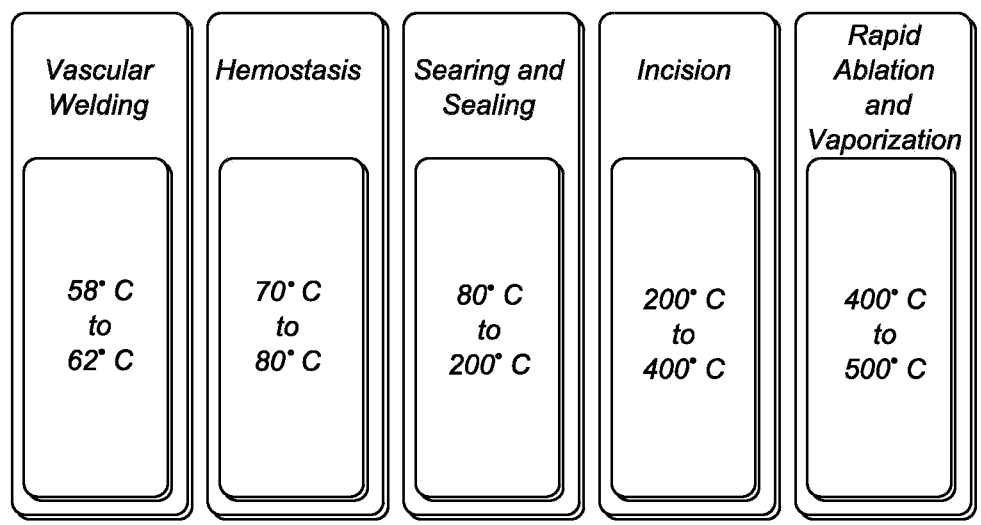
FIG. 29 shows a chart correlating estimated tissue effects with temperature.

FIG. 28 shows a side view of an alternate embodiment of a surgical instrument 335 made in accordance with principles of the present invention. The instrument 335 is configured with a parallel movement linkage to keep the active surfaces parallel to one another. The parallel linkage may include a direct linkage 340. As the trigger 290 is squeezed, the linkage 340 may rotate, advance or otherwise cause a movable tip 370 to approach a stationary tip 360. As the trigger is released, the movable tip 370 may withdraw from the stationary tip 360.

The instrument 335 may include one or more active surfaces 40 on tips 360, 370. The active surfaces 40 may apply pressure to seal and cut tissue, including ducts such as blood vessels, fallopian tubes, etc., as described above.

While not shown in all of FIGS. 22 through 28, will be appreciated that thermally active elements would be disposed on opposing sides of the tips and would be disposed in communication with a power source to selectively heat the active elements.

Turning now to FIG. 29, a chart correlating estimated tissue effects with temperature is shown. It should be recognized that these temperature ranges are estimates, and that temperatures may vary depending on multiple factors that may include tissue type, tissue make-up, and water content. Vascular welding is estimated to occur near the range of 58° C. to 62° C. Hemostasis is estimated to occur near the range of 70° C. and 80° C. Searing and sealing is estimated to occur near the range of 80° C. and 200° C. Incision is estimated to occur near the range of 200° C. and 400° C. Rapid ablation and vaporization is estimated to occur near the range of 400° C. and 500° C.

It will be appreciated that the surgical instrument of the present invention has a wide variety of uses. As the tips are applied to a piece of tissue, the surgical instrument is aligned with respect to the tissue so as to extend across the area to be sealed and/or cut. The active surfaces will typically firmly engage the tissue and then the physician will activate the thermally active elements to cut and/or seal the tissue. It will be appreciated that the cutting could be done first, or the sealing can be done first, depending on the particular desires of the physician. Alternatively, a surgical instrument could be made in accordance with the present invention that operates with programmed order, such as sealing for a given amount of time and then cutting the tissue without the physician having to activate each step.

It will also be appreciated that respective elements can be heated to seal and/or cut the tissue. While it is preferred that the active surfaces be parallel and very close to one another, it will be appreciated that such is not necessary in accordance with the principles of the present invention.

There is thus disclosed an improved tissue cutting and sealing instrument. It will be appreciated that numerous changes may be made to the present invention without departing from the scope of the claims.

What is claimed is:

1. A surgical instrument, comprising:
   a first arm having a first proximal end and a first distal end, the first distal end spaced from the first proximal end in a distal direction;
   a second arm having a second proximal end and a second distal end, the second distal end spaced from the second proximal end in the distal direction, the second arm having a surface that faces the first arm, and the second arm physically coupled to the first arm such that the first arm and the second arm are movable toward one another;
   a ferromagnetic heater forming a rigid loop, the rigid loop physically coupled to and extending from the first arm in the distal direction; and
   a sensor physically coupled to the surface of the second arm at a position distal of the first distal end with respect to the distal direction and aligned with the rigid loop with respect to a direction perpendicular to the distal direction, wherein the sensor monitors at least one property of tissue positioned between the ferromagnetic heater and the sensor.

2. The surgical instrument of claim 1 wherein the ferromagnetic heater includes a conductor and a ferromagnetic material disposed about the conductor, the conductor coupleable to an electrical power source, wherein electrical power passing through the conductor causes the ferromagnetic material to heat.

3. The surgical instrument of claim 2, further comprising:
a cable that couples the conductor to the electrical power source.

4. The surgical instrument of claim 1 wherein the sensor comprises a temperature sensor.

5. The surgical instrument of claim 1 wherein the sensor monitors a change in a standing wave ratio of electrical energy applied to the tissue via the ferromagnetic heater.

6. The surgical instrument of claim 1 wherein the sensor monitors at least one of conductivity, moisture content and impedance of the tissue positioned between the ferromagnetic heater and the sensor.

7. The surgical instrument of claim 1 wherein the sensor provides an indication of a transition from one of a sealing procedure and a cutting procedure to the other of a sealing procedure and a cutting procedure.

8. The surgical instrument of claim 1 wherein the sensor provides a status indication of at least one of a sealing procedure and a cutting procedure.

9. The surgical instrument of claim 8, further comprising:
a power supply that supplies electrical power to the ferromagnetic heater, the power supply communicatively coupled to the sensor, the power supply automatically adjusts the electrical power supplied to the ferromagnetic heater based on the status indication provided by the sensor.

10. A method of treating tissue, comprising:
positioning tissue between a ferromagnetic heater that is physically coupled to a distal region of a first arm of a surgical instrument and a sensor that is physically coupled to a distal region of a second arm of the surgical instrument, the first arm and the second arm physically coupled to one another;
moving the distal region of the first arm and the distal region of the second arm toward one another to bring the ferromagnetic heater and the sensor into contact with the tissue;
delivering electrical energy to the ferromagnetic heater to apply heat to the tissue;
while applying heat to the tissue, providing line of sight to a portion of the tissue that is being heated by the ferromagnetic heater, the line of sight passing through an opening formed by the ferromagnetic heater and the first arm; and
monitoring, by the sensor, at least one property of the tissue while the ferromagnetic heater applies heat to the tissue.

11. The method of claim 10 wherein delivering electrical energy to the ferromagnetic heater comprises delivering the electrical energy through a conductor and heating a ferromagnetic material disposed about the conductor.

12. The method of claim 10 wherein delivering electrical energy to the ferromagnetic heater comprises coupling the ferromagnetic heater to a power source in a closed circuit.

13. The method of claim 10 wherein monitoring the at least one property of the tissue comprises monitoring a temperature of the tissue.

14. The method of claim 10 wherein monitoring the at least one property of the tissue comprises monitoring at least one of: conductivity, moisture content and impedance of the tissue.

15. The method of claim 10, further comprising:
providing, by the sensor, a status indication of at least one of a sealing procedure and a cutting procedure.

16. The method of claim 15, further comprising:
automatically adjusting the delivered electrical power based on the status indication provided by the sensor.

17. The method of claim 10 wherein moving the distal region of the first arm and the distal region of the second arm toward one another includes moving a surface of the second arm toward the first arm, wherein the surface both faces toward the first arm and carries the sensor.

* * * * *